(12) United States Patent
Shigemori et al.

(10) Patent No.: US 7,902,335 B1
(45) Date of Patent: Mar. 8, 2011

(54) HEAT-STABLE RECA MUTANT PROTEIN AND A NUCLEIC ACID AMPLIFICATION METHOD USING THE HEAT-STABLE RECA MUTANT PROTEIN

(75) Inventors: Yasushi Shigemori, Kisarazu (JP); Takehiko Shibata, Wako (JP); Tsutomu Mikawa, Wako (JP)

(73) Assignees: Aisin Seiki Kabushiki Kaisha, Kariya-shi (JP); Riken, Wako-shi (JP)

( * ) Notice: Subject to any disclaimer, the term of this patent is extended or adjusted under 35 U.S.C. 154(b) by 625 days.

(21) Appl. No.: 11/780,284

(22) Filed: Jul. 19, 2007

(30) Foreign Application Priority Data

Jul. 26, 2006 (JP) ................................. 2006-203810

(51) Int. Cl.
*C07K 14/00* (2006.01)
*C07H 21/02* (2006.01)
*C12P 21/04* (2006.01)

(52) U.S. Cl. ......................... 530/350; 536/23.1; 435/71.1

(58) Field of Classification Search .................. None
See application file for complete search history.

(56) References Cited

U.S. PATENT DOCUMENTS

| | | | |
|---|---|---|---|
| 5,510,473 | A | 4/1996 | Camerini-Otero et al. |
| 2004/0081963 | A1 | 4/2004 | Wang |
| 2005/0136443 | A1 | 6/2005 | Shigemori |
| 2005/0260631 | A1 | 11/2005 | Shigemori et al. |
| 2007/0092896 | A1 | 4/2007 | Shigemori et al. |

FOREIGN PATENT DOCUMENTS

| | | |
|---|---|---|
| EP | 1 522 597 A1 | 4/2005 |
| WO | WO 2004/037979 A2 | 5/2004 |

OTHER PUBLICATIONS

Wetmur et al., Cloning, sequencing, and expression of RecA proteins from three distantly related thermophilic eubacteria., J Biol Chem, 1994, vol. 269, pp. 25928-25935.*

Shigemori et al., Multiplex PCR: use of heat-stable *Thermus thermophilus* RecA protein to minimize non-specific PCR products, Nucleic Acid Research 2005, vol. 33(14), pp. 1-9.*

Celia Perales, et al., "Enhancement of DNA, cDNA synthesis and fidelity at high temperatures by a dimeric single-stranded DNA-binding protein", Nucleic Acids Research, vol. 31, No. 22, 2003, pp. 6473-6480.

Quin Chou, "Minimizing deletion mutagenesis artifact during Taq DNA polymerase PCR by *E. coli* SSB", Nucleic Acids Research, vol. 20, No. 16, May 28, 1992, p. 4371.

Rapley R., "Enhancing PCR amplification and sequencing using DNA-binding proteins", Mol Biotechnol, 2(3), Dec. 1994, p. 295-8.

"iProof High-Fidelity DNA Polymerase", Bio-Rad Laboratories Inc., 3 pages. last viewed on Jan. 6, 2006.

Yasushi Shigemori, et al., "Multiplex PCR: use of heat-stable Thermus thermophilus RecA protein to minimize non-specific PCR products", Nucleic Acids Research, vol. 33, No. 14, e126, 2005, 9 pages.

* cited by examiner

*Primary Examiner* — Alexander D Kim
(74) *Attorney, Agent, or Firm* — Oblon, Spivak, McClelland, Maier & Neustadt, L.L.P.

(57) ABSTRACT

A heat-stable RecA mutant protein is obtained by mutation involving either deletion or substitution of at least one amino acid in an amino acid sequence composing an acid region at C-terminal end of a wild type heat-stable RecA protein, and has an improved ability, compared to the wild type heat-stable RecA protein, for contributing to an increase in an amplification specificity of a template nucleic acid in a nucleic acid amplification reaction.

10 Claims, 9 Drawing Sheets

```
Frozen cell 50g
200ml TS buffer addition ( on ice)
Lysozyme addition (final concentration 0.5mg/ml)
Brij58 addition (final concentration 0.4%)
Ultrasonic treatment (1 minute×3~5 times, on ice)
EDTA addition (final concentration 5mM)
KCl addition (final concentration 1M, ~280ml)
Centrifugal separation (60,000g 60 minutes, 4°C)
Supernatant harvest
Thermal treatment (65°C, 60 minutes)
Centrifugal separation (60,000g 20 minutes)
Supernatant harvest
Ammonium sulfate addition (final concentration 0.8M)
Butyl Toyopearl (200ml,TEM0.8AS buffer)
Application of protein solution
Washing with PEM0.8 AS buffer (300ml)
    ↓
Elution with PEM buffer (200ml)
Collection of all peaks
Dialysis with PEM buffer (~2 times)
CM52 column (300ml,PEM buffer)
Application of protein solution
Washing with PEM0.3K buffer (450ml)
Elution with PEMK buffer (300ml)
Collection of all peaks
Dialysis with PEM buffer (20 hours)
P11 column (300ml,PEM buffer)
Application of protein solution
Cleaning with PEM buffer (450ml)
Elution with PEM buffer (300ml)
Collection of all peaks
Dialysis with TEDG buffer (20 hours, 4°C)
    ↓
Storage at -20°C
```

FIG. 1

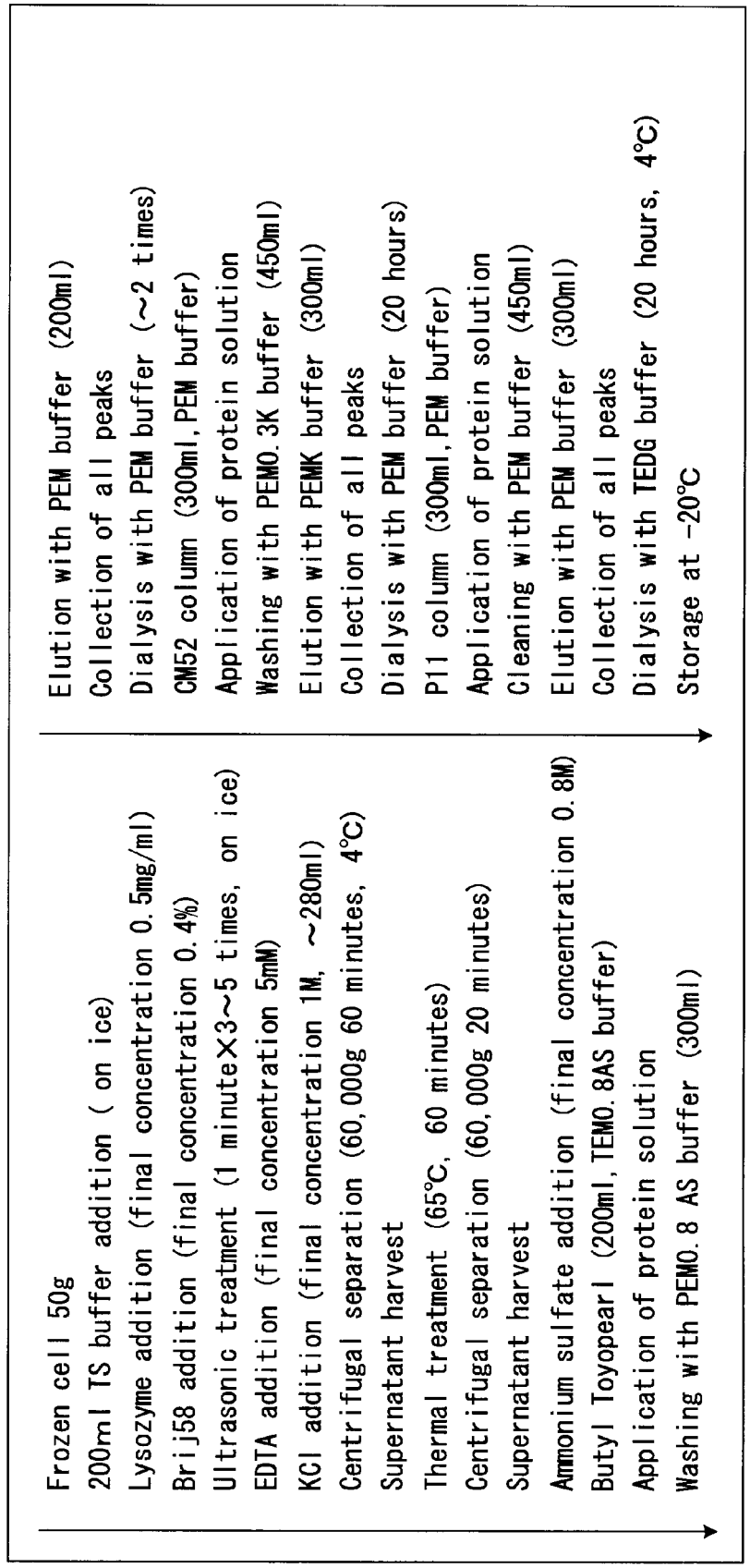

Frozen cell 50g
200ml TS buffer addition (on ice)
Lysozyme addition (final concentration 0.5mg/ml)
Brij58 addition (final concentration 0.4%)
Ultrasonic treatment (1 minute×3~5 times, on ice)
EDTA addition (final concentration 5mM)
KCl addition (final concentration 1M, ~280ml)
Centrifugal separation (60,000g 60 minutes, 4°C)
Supernatant harvest
Thermal treatment (65°C, 60 minutes)
Centrifugal separation (60,000g 20 minutes)
Supernatant harvest
Ammonium sulfate addition (final concentration 0.8M)
Butyl Toyopearl (200ml, TEM0.8AS buffer)
Application of protein solution
Washing with PEM0.8 AS buffer (300ml)
Elution with PEM buffer (200ml)
Collection of all peaks
Dialysis with PEM buffer (~2 times)
CM52 column (300ml, PEM buffer)
Application of protein solution
Washing with PEM0.3K buffer (450ml)
Elution with PEMK buffer (300ml)
Collection of all peaks
Dialysis with PEM buffer (20 hours)
P11 column (300ml, PEM buffer)
Application of protein solution
Cleaning with PEM buffer (450ml)
Elution with PEM buffer (300ml)
Collection of all peaks
Dialysis with TEDG buffer (20 hours, 4°C)
Storage at −20°C

FIG. 2

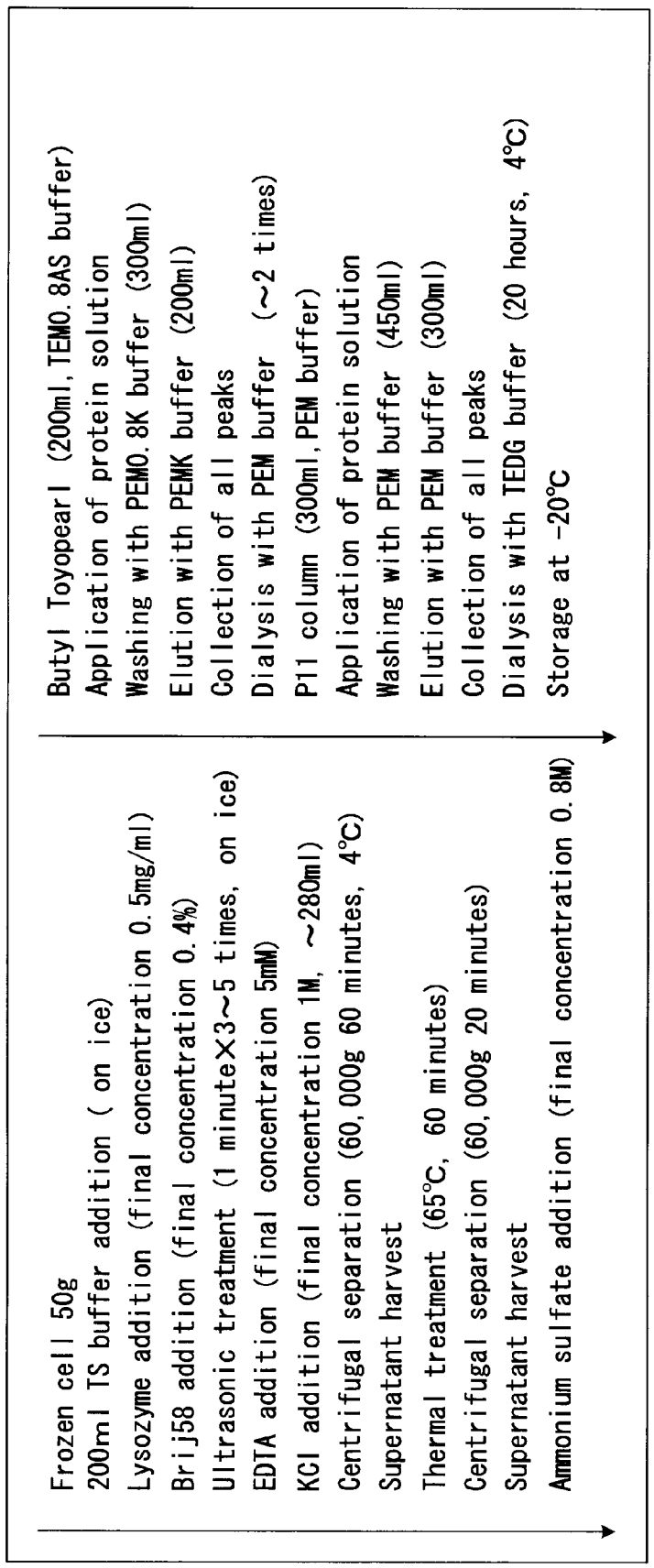

Frozen cell 50g
200ml TS buffer addition (on ice)
Lysozyme addition (final concentration 0.5mg/ml)
Brij58 addition (final concentration 0.4%)
Ultrasonic treatment (1 minute×3~5 times, on ice)
EDTA addition (final concentration 5mM)
KCl addition (final concentration 1M, ~280ml)
Centrifugal separation (60,000g 60 minutes, 4°C)
Supernatant harvest
Thermal treatment (65°C, 60 minutes)
Centrifugal separation (60,000g 20 minutes)
Supernatant harvest
Ammonium sulfate addition (final concentration 0.8M)
Butyl Toyopearl (200ml, TEM0.8AS buffer)
Application of protein solution
Washing with PEM0.8K buffer (300ml)
Elution with PEMK buffer (200ml)
Collection of all peaks
Dialysis with PEM buffer (~2 times)
P11 column (300ml, PEM buffer)
Application of protein solution
Washing with PEM buffer (450ml)
Elution with PEM buffer (300ml)
Collection of all peaks
Dialysis with TEDG buffer (20 hours, 4°C)
Storage at -20°C

FIG. 3

Structure of wild type heat stable RecA protein
(amino acid sequence)

MDESKRKALENALKAIEKEFGKGAVMRLGEMPKQQVDVIPTGSLALDLALGIGGIP
RGRIVEIYGPESGGKTTLALTIIAQAQRRGGVAAFVDAEHALDPLYAQRLGVQVEDLL
VSQPDTGEQALEIVELLARSGAVDVIVVDSVAALVPRAEIEGEMGDQHVGLQARLMS
QALRKLTAVLAKSNTAAIFINQVREKVGVTYGNPETTPGGRALKFYASVRLDVRKSG
QPIKVGNEAVGVKVRVKVVKNKLAPPFREAELEIYFGRGLDPVADLVNVAVAAGVIE
KAGSWFSYGELRLGQGKEKAAEALRERPELLEEIRAKVLERS–DQVVLAAGEDEGE

Amino acid is cut here

Structure of heat stable RecA mutant protein (Hyper-TthRecA protein)
(amino acid sequence)

MDESKRKALENALKAIEKEFGKGAVMRLGEMPKQQVDVIPTGSLALDLALGIGGIP
RGRIVEIYGPESGGKTTLALTIIAQAQRRGGVAAFVDAEHALDPLYAQRLGVQVEDLL
VSQPDTGEQALEIVELLARSGAVDVIVVDSVAALVPRAEIEGEMGDQHVGLQARLMS
QALRKLTAVLAKSNTAAIFINQVREKVGVTYGNPETTPGGRALKFYASVRLDVRKSG
QPIKVGNEAVGVKVRVKVVKNKLAPPFREAELEIYFGRGLDPVADLVNVAVAAGVIE
KAGSWFSYGELRLGQGKEKAAEALRERPELLEEIRAKVLERS

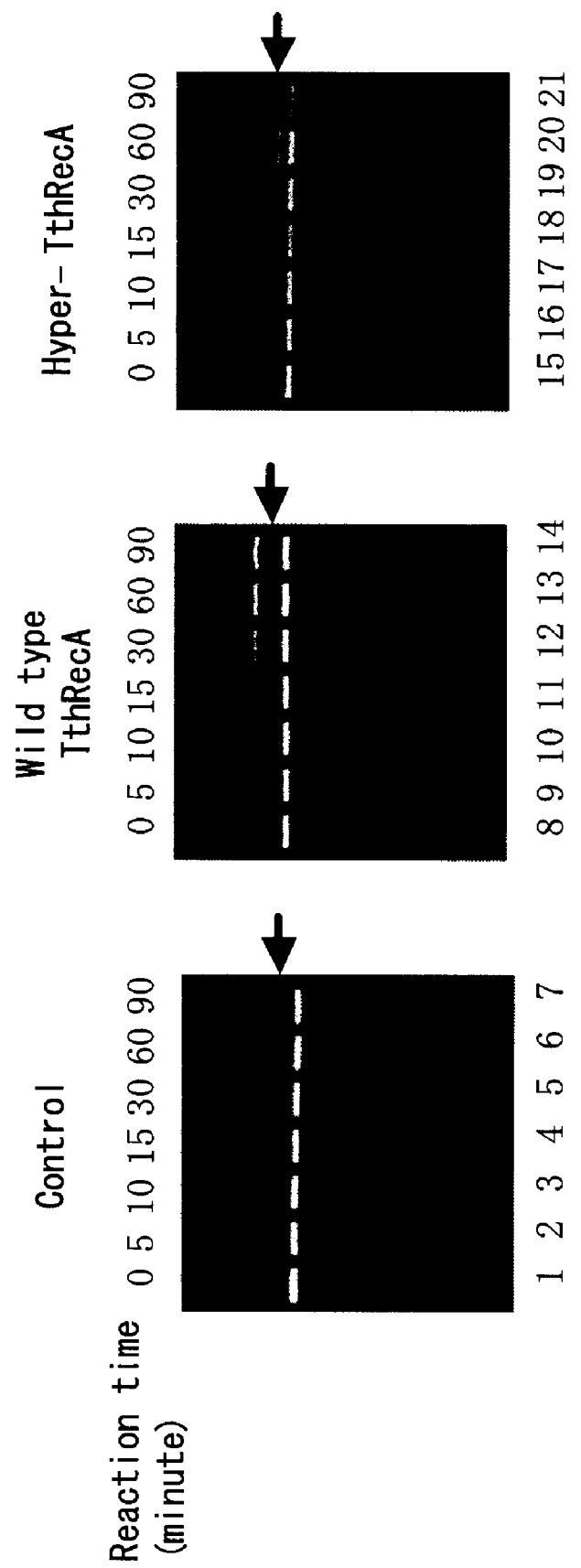
F I G. 5

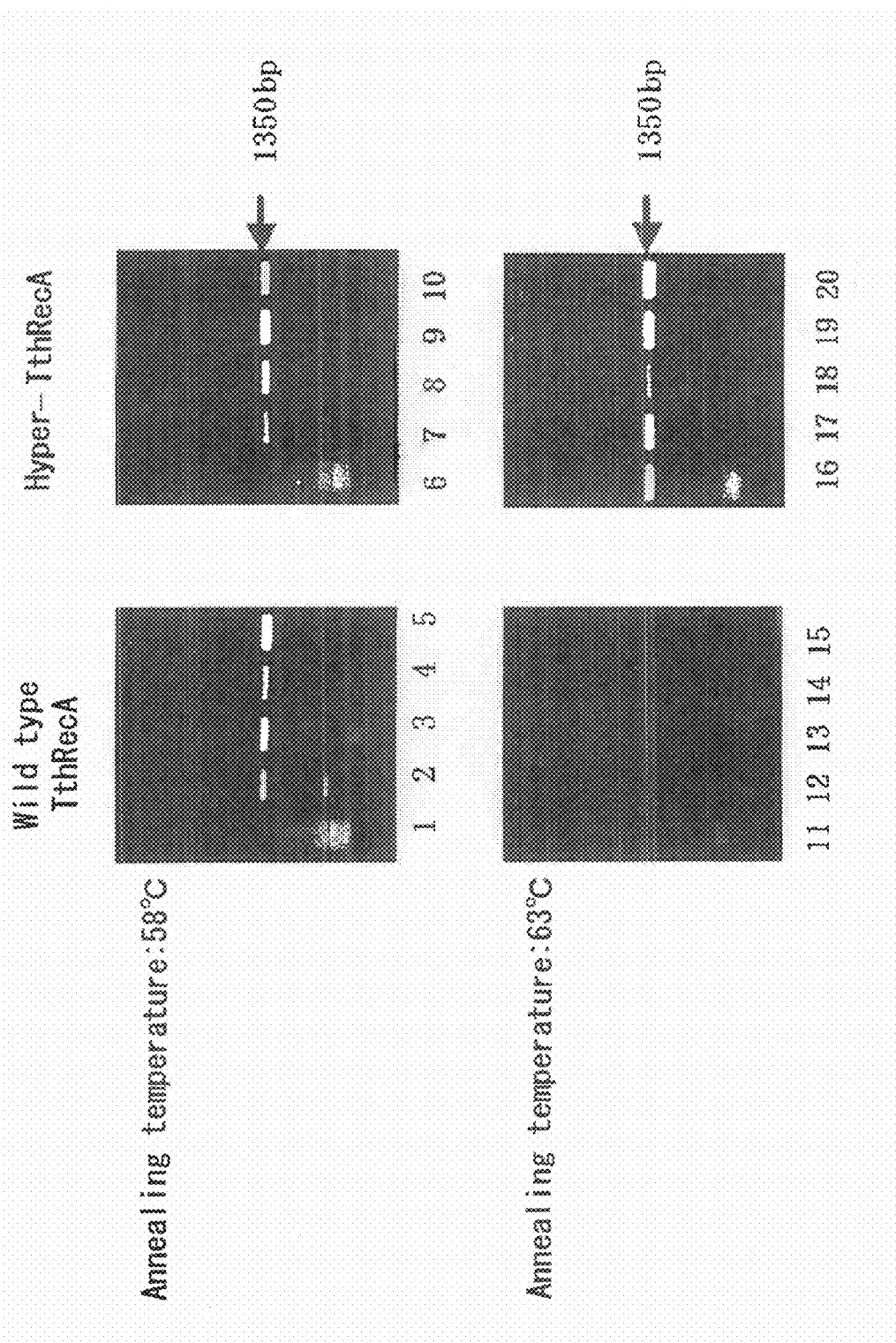

SEQUENCE LISTING

```
<160> NUMBER OF SEQ ID NOS: 27

<210> SEQ ID NO 1
<211> LENGTH: 1008
<212> TYPE: DNA
<213> ORGANISM: Thermus thermophilus

<400> SEQUENCE: 1
atggacgaga gcaagcgcaa ggccctggag aacgccctga aggcgattga gaaggagttc        60
ggcaaggggg cggtgatgcg gctgggcgag atgcccaagc agcaggtgga cgtgatcccc       120
accggctccc tcgccctaga cctcgccctg gggatcggcg gcatccccg ggggcggatc        180 gtggagatct atgcccccga gtccggggc aagaccaccc tcgccctcac catcatcgcc        240
caggcccaga ggcggggcgg ggtggccgcc ttcgtggatg cggagcacgc cctggacccc      300
ctgtacgccc agcgcctcgg cgtccaggtg gaggacctcc tggtctccca gcccgacacg      360
ggcgagcagg ccctggagat cgtggagctc ctcgcccgct cggggcggt ggacgtgatc        420 gtggtggact cggtggccgc cttggtcccc ggggcggaga ttgaggggga gatggggac        480 cagcacgtgg gcctccaggc ccggctcatg agccaggccc tccgcaagct caccgcggtg      540
ctcgccaaga gcaacaccgc cgccatcttc atcaaccagg tgcgggagaa ggtgggggtc      600
acgtacggca accccgagac caccccgggg gggagggcgc tgaagttcta cgccagcgtg      660
cgcctggacg tgcgcaaaag cggccagccc atcaaggtgg ggaacgaggc cgtgggcgtc      720
```

```
aaggtgcggg tcaaggtggt gaagaacaag ctcgccccccc ccttccgcga ggcggagctg    780
gagatctact tcggccgggg cctggacccg gtggccgacc tggtgaacgt ggccgtggcc    840 gcggggtca ttgagaaggc cgggtcctgg ttctcctacg ggagctccg cctgggccag      900 gggaaggaga aggcggccga ggccctgcgg gagcggcccg agcttttgga ggagatccgc    960
gccaaggtct tggagcgctc ggaccaggtg gtcctggccg cgggctaa               1008
```

```
<210> SEQ ID NO 2
<211> LENGTH: 327
<212> TYPE: PRT
<213> ORGANISM: Thermus thermophilus

<400> SEQUENCE: 2

Met Asp Glu Ser Lys Arg Lys Ala Leu Glu Asn Ala Leu Lys Ala Ile
1               5                   10                  15

Glu Lys Glu Phe Gly Lys Gly Ala Val Met Arg Leu Gly Glu Met Pro
                20                  25                  30

Lys Gln Gln Val Asp Val Ile Pro Thr Gly Ser Leu Ala Leu Asp Leu
            35                  40                  45

Ala Leu Gly Ile Gly Gly Ile Pro Arg Gly Arg Ile Val Glu Ile Tyr
50                  55                  60

Gly Pro Glu Ser Gly Gly Lys Thr Thr Leu Ala Leu Thr Ile Ile Ala
65                  70                  75                  80

Gln Ala Gln Arg Arg Gly Gly Val Ala Ala Phe Val Asp Ala Glu His
                85                  90                  95

Ala Leu Asp Pro Leu Tyr Ala Gln Arg Leu Gly Val Gln Val Glu Asp
            100                 105                 110

Leu Leu Val Ser Gln Pro Asp Thr Gly Glu Gln Ala Leu Glu Ile Val
        115                 120                 125

Glu Leu Leu Ala Arg Ser Gly Ala Val Asp Val Ile Val Val Asp Ser
130                 135                 140

Val Ala Ala Leu Val Pro Gly Ala Glu Ile Glu Gly Glu Met Gly Asp
145                 150                 155                 160

Gln His Val Gly Leu Gln Ala Arg Leu Met Ser Gln Ala Leu Arg Lys
                165                 170                 175

Leu Thr Ala Val Leu Ala Lys Ser Asn Thr Ala Ala Ile Phe Ile Asn
            180                 185                 190

Gln Val Arg Glu Lys Val Gly Val Thr Tyr Gly Asn Pro Glu Thr Thr
        195                 200                 205

Pro Gly Gly Arg Ala Leu Lys Phe Tyr Ala Ser Val Arg Leu Asp Val
210                 215                 220

Arg Lys Ser Gly Gln Pro Ile Lys Val Gly Asn Glu Ala Val Gly Val
225                 230                 235                 240

Lys Val Arg Val Lys Val Val Lys Asn Lys Leu Ala Pro Pro Phe Arg
                245                 250                 255

Glu Ala Glu Leu Glu Ile Tyr Phe Gly Arg Gly Leu Asp Pro Val Ala
            260                 265                 270

Asp Leu Val Asn Val Ala Val Ala Ala Gly Val Ile Glu Lys Ala Gly
        275                 280                 285

Ser Trp Phe Ser Tyr Gly Glu Leu Arg Leu Gly Gln Gly Lys Glu Lys
290                 295                 300

Ala Ala Glu Ala Leu Arg Glu Arg Pro Glu Leu Leu Glu Glu Ile Arg
305                 310                 315                 320

Ala Lys Val Leu Glu Arg Ser
                325
```

<210> SEQ ID NO 3
<211> LENGTH: 1085
<212> TYPE: DNA
<213> ORGANISM: Thermus thermophilus

<400> SEQUENCE: 3

```
ggggcccggt gtacatgttt tggagaagtt ttccctgaga ggtgagcatg gacgagagca      60
agcgcaaggc cctggagaac gccctgaagg cgattgagaa ggagttcggc aaggggggcgg    120
tgatgcggct gggcgagatg cccaagcagc aggtggacgt gatccccacc ggctccctcg    180
ccctagacct cgccctgggg atcggcggca tccccggggg gcggatcgtg gagatctatg    240
gccccgagtc cgggggcaag accaccctcg ccctcaccat catcgcccag gcccagaggc    300
ggggcggggt ggccgccttc gtggatgcgg agcacgccct ggaccccctg tacgcccagc    360
gcctcggcgt ccaggtggag gacctcctgg tctcccagcc cgacacgggc gagcaggccc    420
tggagatcgt ggagctcctc gcccgctcgg gcggtgga cgtgatcgtg gtggactcgg    480
tggccgcctt ggtccccggg gcggagattg aggggggagat ggggggaccag cacgtgggcc    540
tccaggcccg gctcatgagc caggccctcc gcaagctcac cgcggtgctc gccaagagca    600
acaccgccgc catcttcatc aaccaggtgc gggagaaggt gggggtcacg tacggcaacc    660
ccgagaccac cccgggggg agggcgctga agttctacgc cagcgtgcgc ctggacgtgc    720
gcaaaagcgg ccagcccatc aagtggggga acgaggccgt gggcgtcaag gtgcgggtca    780
aggtggtgaa gaacaagctc gcccccccct tccgcgaggc ggagctggag atctacttcg    840
gccgggccct ggaccggtg gccgacctgg tgaacgtggc cgtggccgcg ggggtcattg    900
agaaggccgg gtcctggttc tcctacgggg agctccgcct gggccagggg aaggagaagg    960
cggccgaggc cctgcgggag cggcccgagc tttttggagga gatccgcgcc aaggtcttgg   1020
agcgctcgga ccaggtggtc ctggccgcgg gcgaggacga ggggggagtag atgtcccttc   1080
tggac                                                              1085
```

<210> SEQ ID NO 4
<211> LENGTH: 340
<212> TYPE: PRT
<213> ORGANISM: Thermus thermophilus

<400> SEQUENCE: 4

```
Met Asp Glu Ser Lys Arg Lys Ala Leu Glu Asn Ala Leu Lys Ala Ile
1               5                   10                  15

Glu Lys Glu Phe Gly Lys Gly Ala Val Met Arg Leu Gly Glu Met Pro
            20                  25                  30

Lys Gln Gln Val Asp Val Ile Pro Thr Gly Ser Leu Ala Leu Asp Leu
        35                  40                  45

Ala Leu Gly Ile Gly Gly Ile Pro Arg Gly Arg Ile Val Glu Ile Tyr
    50                  55                  60

Gly Pro Glu Ser Gly Gly Lys Thr Thr Leu Ala Leu Thr Ile Ile Ala
65                  70                  75                  80

Gln Ala Gln Arg Arg Gly Gly Val Ala Ala Phe Val Asp Ala Glu His
                85                  90                  95

Ala Leu Asp Pro Leu Tyr Ala Gln Arg Leu Gly Val Gln Val Glu Asp
            100                 105                 110

Leu Leu Val Ser Gln Pro Asp Thr Gly Glu Gln Ala Leu Glu Ile Val
        115                 120                 125

Glu Leu Leu Ala Arg Ser Gly Ala Val Asp Val Ile Val Val Asp Ser
    130                 135                 140
```

-continued

Val Ala Ala Leu Val Pro Gly Ala Glu Ile Glu Gly Glu Met Gly Asp
145                 150                 155                 160

Gln His Val Gly Leu Gln Ala Arg Leu Met Ser Gln Ala Leu Arg Lys
                165                 170                 175

Leu Thr Ala Val Leu Ala Lys Ser Asn Thr Ala Ala Ile Phe Ile Asn
            180                 185                 190

Gln Val Arg Glu Lys Val Gly Val Thr Tyr Gly Asn Pro Glu Thr Thr
        195                 200                 205

Pro Gly Gly Arg Ala Leu Lys Phe Tyr Ala Ser Val Arg Leu Asp Val
    210                 215                 220

Arg Lys Ser Gly Gln Pro Ile Lys Val Gly Asn Glu Ala Val Gly Val
225                 230                 235                 240

Lys Val Arg Val Lys Val Lys Asn Lys Leu Ala Pro Pro Phe Arg
                245                 250                 255

Glu Ala Glu Leu Glu Ile Tyr Phe Gly Arg Gly Leu Asp Pro Val Ala
                260                 265                 270

Asp Leu Val Asn Val Ala Val Ala Ala Gly Val Ile Glu Lys Ala Gly
            275                 280                 285

Ser Trp Phe Ser Tyr Gly Glu Leu Arg Leu Gly Gln Gly Lys Glu Lys
        290                 295                 300

Ala Ala Glu Ala Leu Arg Glu Arg Pro Glu Leu Leu Glu Glu Ile Arg
305                 310                 315                 320

Ala Lys Val Leu Glu Arg Ser Asp Gln Val Val Leu Ala Ala Gly Glu
                325                 330                 335

Asp Glu Gly Glu
            340

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctcatatgg acgagagcaa gcgcaa                                        26

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgcaagctta gcccgcggcc aggacca                                       27

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acaatgggct cactcaccc                                                19

```
<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctaagaccaa tggatagctg                                                    20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctcagcatg gtggtggcat aa                                                 22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cctcatacct tccccccat tt                                                  22

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gactactcta gcgactgtcc atctc                                              25

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gacagccacc agatccaatc                                                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aacctcacaa ccttggctga                                                    20
```

```
<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ttcacaactt aagatttggc                                                 20

<210> SEQ ID NO 15
<211> LENGTH: 150
<212> TYPE: DNA
<213> ORGANISM: Artificial Sequence
<220> FEATURE:
<223> OTHER INFORMATION: Description of Artificial Sequence: Synthetic
      150-mer oligonucleotide having pBR322 DNA partial sequence

<400> SEQUENCE: 15
tgttgtgcaa aaaagcggtt agctccttcg gtcctccgat cgttgtcaga agtaagttgg     60
ccgcagtgtt atcactcatg gttatggcag cactgcataa ttctcttact gtcatgccat    120
ccgtaagatg cttttctgtg actggtgagt                                     150

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
taataaactt gttcccagat                                                 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aggagaaaga gcagtgggag                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gataagtgga actttagtgt                                                 20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cataagcatt acactgcgca                                                 20
```

```
<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atacctaagg ctctactgca                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aggcaatggc ggcacccatc                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atttctggcc tccaacgtta                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccagaaatgc aggcaattgt                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgagccccat cctgaattcc                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cagaatggtt gtgtagcgca                                              20
```

```
<210> SEQ ID NO 26
<211> LENGTH: 327
<212> TYPE: PRT
<213> ORGANISM: Thermus thermophilus

<400> SEQUENCE: 26

Met Asp Glu Ser Lys Arg Lys Ala Leu Glu Asn Ala Leu Lys Ala Ile
1               5                   10                  15

Glu Lys Glu Phe Gly Lys Gly Ala Val Met Arg Leu Gly Glu Met Pro
            20                  25                  30

Lys Gln Gln Val Asp Val Ile Pro Thr Gly Ser Leu Ala Leu Asp Leu
        35                  40                  45

Ala Leu Gly Ile Gly Gly Ile Pro Arg Gly Arg Ile Val Glu Ile Tyr
    50                  55                  60

Gly Pro Glu Ser Gly Gly Lys Thr Thr Leu Ala Leu Thr Ile Ile Ala
65                  70                  75                  80

Gln Ala Gln Arg Arg Gly Gly Val Ala Ala Phe Val Asp Ala Glu His
                85                  90                  95

Ala Leu Asp Pro Leu Tyr Ala Gln Arg Leu Gly Val Gln Val Glu Asp
            100                 105                 110

Leu Leu Val Ser Gln Pro Asp Thr Gly Glu Gln Ala Leu Glu Ile Val
        115                 120                 125

Glu Leu Leu Ala Arg Ser Gly Ala Val Asp Val Ile Val Val Asp Ser
    130                 135                 140

Val Ala Ala Leu Val Pro Arg Ala Glu Ile Glu Gly Glu Met Gly Asp
145                 150                 155                 160

Gln His Val Gly Leu Gln Ala Arg Leu Met Ser Gln Ala Leu Arg Lys
                165                 170                 175

Leu Thr Ala Val Leu Ala Lys Ser Asn Thr Ala Ala Ile Phe Ile Asn
            180                 185                 190

Gln Val Arg Glu Lys Val Gly Val Thr Tyr Gly Asn Pro Glu Thr Thr
        195                 200                 205

Pro Gly Gly Arg Ala Leu Lys Phe Tyr Ala Ser Val Arg Leu Asp Val
    210                 215                 220

Arg Lys Ser Gly Gln Pro Ile Lys Val Gly Asn Glu Ala Val Gly Val
225                 230                 235                 240

Lys Val Arg Val Lys Val Val Lys Asn Lys Leu Ala Pro Pro Phe Arg
                245                 250                 255

Glu Ala Glu Leu Glu Ile Tyr Phe Gly Arg Gly Leu Asp Pro Val Ala
            260                 265                 270

Asp Leu Val Asn Val Ala Val Ala Gly Val Ile Glu Lys Ala Gly
        275                 280                 285

Ser Trp Phe Ser Tyr Gly Glu Leu Arg Leu Gly Gln Gly Lys Glu Lys
    290                 295                 300

Ala Ala Glu Ala Leu Arg Glu Arg Pro Glu Leu Leu Glu Glu Ile Arg
305                 310                 315                 320

Ala Lys Val Leu Glu Arg Ser
                325

<210> SEQ ID NO 27
<211> LENGTH: 340
<212> TYPE: PRT
<213> ORGANISM: Thermus thermophilus
```

```
<400> SEQUENCE: 27

Met Asp Glu Ser Lys Arg Lys Ala Leu Glu Asn Ala Leu Lys Ala Ile
1               5                   10                  15

Glu Lys Glu Phe Gly Lys Gly Ala Val Met Arg Leu Gly Glu Met Pro
            20                  25                  30

Lys Gln Gln Val Asp Val Ile Pro Thr Gly Ser Leu Ala Leu Asp Leu
                35                  40                  45

Ala Leu Gly Ile Gly Gly Ile Pro Arg Gly Arg Ile Val Glu Ile Tyr
        50                  55                  60

Gly Pro Glu Ser Gly Gly Lys Thr Thr Leu Ala Leu Thr Ile Ile Ala
65                  70                  75                  80

Gln Ala Gln Arg Arg Gly Gly Val Ala Ala Phe Val Asp Ala Glu His
                85                  90                  95

Ala Leu Asp Pro Leu Tyr Ala Gln Arg Leu Gly Val Gln Val Glu Asp
                100                 105                 110

Leu Leu Val Ser Gln Pro Asp Thr Gly Glu Gln Ala Leu Glu Ile Val
                115                 120                 125

Glu Leu Leu Ala Arg Ser Gly Ala Val Asp Val Ile Val Val Asp Ser
130                 135                 140

Val Ala Ala Leu Val Pro Arg Ala Glu Ile Glu Gly Glu Met Gly Asp
145                 150                 155                 160

Gln His Val Gly Leu Gln Ala Arg Leu Met Ser Gln Ala Leu Arg Lys
                165                 170                 175

Leu Thr Ala Val Leu Ala Lys Ser Asn Thr Ala Ala Ile Phe Ile Asn
                180                 185                 190

Gln Val Arg Glu Lys Val Gly Val Thr Tyr Gly Asn Pro Glu Thr Thr
                195                 200                 205

Pro Gly Gly Arg Ala Leu Lys Phe Tyr Ala Ser Val Arg Leu Asp Val
                210                 215                 220

Arg Lys Ser Gly Gln Pro Ile Lys Val Gly Asn Glu Ala Val Gly Val
225                 230                 235                 240

Lys Val Arg Val Lys Val Val Lys Asn Lys Leu Ala Pro Pro Phe Arg
                245                 250                 255

Glu Ala Glu Leu Glu Ile Tyr Phe Gly Arg Gly Leu Asp Pro Val Ala
                260                 265                 270

Asp Leu Val Asn Val Ala Val Ala Ala Gly Val Ile Glu Lys Ala Gly
                275                 280                 285

Ser Trp Phe Ser Tyr Gly Glu Leu Arg Leu Gly Gln Gly Lys Glu Lys
                290                 295                 300

Ala Ala Glu Ala Leu Arg Glu Arg Pro Glu Leu Leu Glu Glu Ile Arg
305                 310                 315                 320

Ala Lys Val Leu Glu Arg Ser Asp Gln Val Val Leu Ala Ala Gly Glu
                325                 330                 335

Asp Glu Gly Glu
                340
```

HEAT-STABLE RECA MUTANT PROTEIN AND A NUCLEIC ACID AMPLIFICATION METHOD USING THE HEAT-STABLE RECA MUTANT PROTEIN

CROSS REFERENCE TO RELATED APPLICATIONS

This application is based on and claims priority under 35 U.S.C §119 with respect to Japanese Patent Application 2006-203810, filed on Jul. 26, 2006, the entire content of which is incorporated herein by reference.

FIELD OF THE INVENTION

This invention relates to a heat-stable RecA mutant protein and a use thereof. In particular, the invention relates to a heat-stable RecA mutant protein which improves an ability, compared with a wild type heat-stable RecA protein, to contribute to an increase in an amplification specificity of a template nucleic acid in a nucleic acid amplification reaction, and a use thereof.

BACKGROUND

Nucleic acid amplification techniques such as polymerase chain reaction (the reaction may be abbreviated to PCR hereinafter) are innovative in that the techniques are able to amplify a target DNA region 100,000 times or more in a short time. However, it is difficult to optimize the reaction. There is a technical issue that the amplification specificity is reduced by non-specific amplification caused by mis-annealing of the primer such as annealing the primer to sites other than the target sequence or annealing between primers. The amplification product which is not specific to a template nucleic acid could be a factor to reduce the amplification specificity and cause background noise to affect experiments to be conducted later. Therefore, it is required to establish an amplification technique having high accuracy for restraining the non-specific amplification and specifically amplifying a target nucleic acid.

A variety of attempts are reported for controlling the reaction to prevent the mis-annealing of the primer at each step of the amplification cycle. Specifically, it has been reported that the nucleic acid amplification specificity is improved by carrying out PCR in the presence of single strand binding proteins (referred as to SSB hereinafter) derived from *Thermus thermophilus*, SSB derived from *E. coli*, or SSB from bacteriophage T4 (refer as to T4gp32 hereinafter) (T4 gene 32 protein, refer to Non patent documents 1, 2, 3). It is also reported that the nucleic acid amplification specificity is improved by carrying out PCR by a DNA polymerase to which a double-stranded DNA binding protein (Sso7d) is bound (for example, refer to Patent document 1 and Non patent document 4). However, these methods do not fully satisfy the needs of the market in terms of the amplification specificity.

Recently, the inventors reported that a RecA protein derived from an extremely thermophilic bacterium can bind to a template or a primer to promote binding of the primer only to a specific template sequence and the mis-annealing of the primer can be restrained thereby (For example, refer to Patent documents 2 and 3, and Non patent document 5). A RecA protein binds to a single-stranded nucleic acid cooperatively, searches a homologous region between the single-stranded nucleic acid and a double-stranded nucleic acid and undergoes homologous recombination of nucleic acids.

However, in the above-method that the inventors reported, it was found that biological functions of the heat-stable RecA protein were not fully achieved depending on the reaction condition and the non-specific amplification might occur. Thus, in order to achieve the high specificity of nucleic acid amplification, an improved technique is still needed for properly controlling the nucleic acid amplification reaction. Also, the nucleic acid amplification reaction requires expensive reagents such as a thermostable DNA polymerase. For this reason, a technique is needed for reducing the amount of the expensive reagents and specifically amplifying the target nucleic acid in an inexpensive manner.

A need exists for a heat-stable RecA mutant protein and a nucleic acid amplification method using the heat-stable RecA mutant protein which are not susceptible to the drawback mentioned above.

Patent Document 1: WO 04/037979
Patent Document 2: U.S. Pat. No. 2005/260631
Patent Document 3: EPO Publication 1522597
Non-Patent Document 1: Perales et al., "Enhancement of DNA, cDNA synthesis and fidelity at high temperatures by a dimeric single-stranded DNA-binding protein." Nucleic Acids Research, Volume 31, 22th, 6473-6480, 2003
Non-Patent Document 2: Chou Q., "Minimizing deletion mutagenesis artifact during Taq DNA polymerase PCR by *E. coli* SSB." Nucleic Acids Research, Volume 20, $16^{th}$ issue, 4371, 1992
Non-Patent Document 3: Rapley R., "Enhancing PCR amplification and sequencing using DNA-binding proteins." Mol. Biotechnol., volume 2, $3^{rd}$ issue, 295-298, 1994
Non-Patent Document 4: "iProof High-Fidelity DNA polymerase" [online], BioRad Laboratories Inc., [Jan. 6, 2006 searched] internet <URL: HYPERLINK
Non-Patent Document 5: Shigemori Y. et al., "Multiplex PCR: use of heat-stable *Thermus thermophilus* RecA protein to minimize non-specific PCR products." Nucleic Acids Research, Volume 33, $14^{th}$ issue, 2005, e126

SUMMARY OF THE INVENTION

According to an aspect of the present invention, a heat-stable RecA mutant protein is obtained by mutation involving either deletion or substitution of at least one amino acid in an amino acid sequence composing an acid region at C-terminal end of a wild type heat-stable RecA protein, and has an improved ability, compared to the wild type heat-stable RecA protein, for contributing to an increase in an amplification specificity of a template nucleic acid in a nucleic acid amplification reaction.

BRIEF DESCRIPTION OF THE DRAWINGS

The foregoing and additional features and characteristics of the present invention will become more apparent from the following detailed description considered with reference to the accompanying drawings, wherein:

FIG. 1 is a figure indicating a preparing method (example 1) a the heat-stable RecA mutant protein of the present invention;

FIG. 2 is a figure indicating a preparing method of the heat-stable RecA mutant protein of the present invention;

FIG. 3 is a figure illustrating an example of design of the heat-stable RecA mutant protein (SEQ ID NO: 26) of the present invention (wild type heat-stable RecA protein disclosed as SEQ ID NO: 27);

FIG. 5 is a figure showing the example 3 for evaluating the nature of the heat-stable RecA mutant protein of the present invention (homologous recombination);

FIG. 9 is a figure showing the example 7 for evaluating the nature of the heat-stable RecA mutant protein of the present invention (annealing temperature).

DETAILED DESCRIPTION

Figure 4:
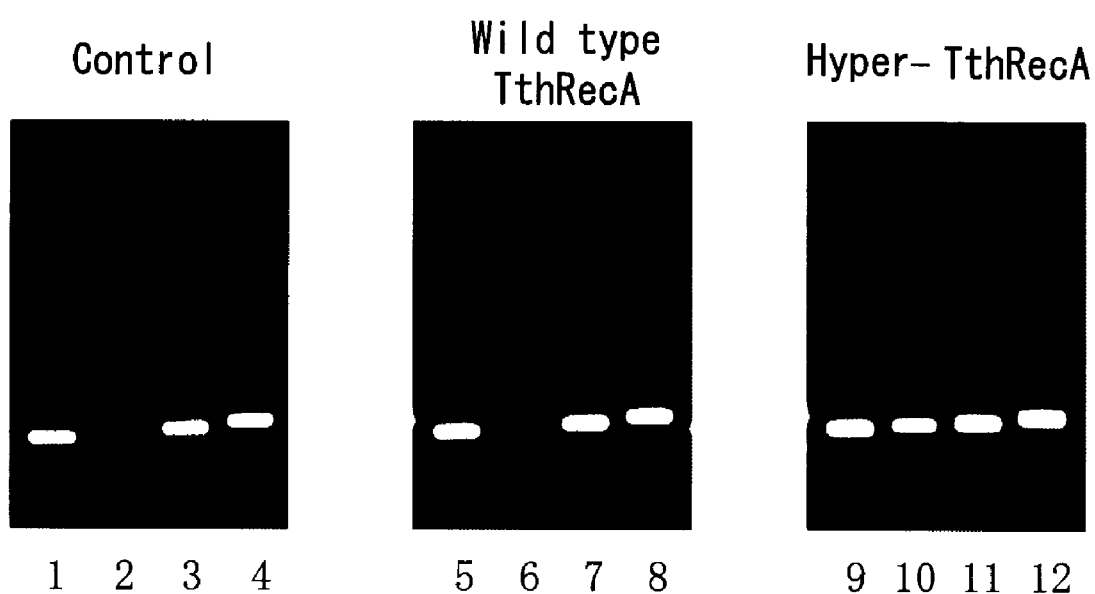
FIG. 4 is a figure showing the example 2 for evaluating the nature of the heat-stable RecA mutant protein of the present invention (reaction specificity)

Specific examples of the present invention will be described below. However, the following examples are intended to illustrate the invention and are not to be construed as being limitations thereon.

Hereinafter, a heat-stable RecA mutant protein of the present invention may be abbreviated to a heat-stable RecA mutant protein. Also, a wild type heat-stable RecA protein of the present invention may be abbreviated to a wild type heat-stable RecA protein.

The heat-stable RecA mutant protein of the present invention includes all heat-stable RecA proteins which express a function for contributing to an increase in an amplification specificity of a template nucleic acid in a nucleic acid amplification reaction. Namely, the heat-stable RecA mutant protein of the present invention is improved in terms of specificity for the template nucleic acid in the nucleic acid amplification reaction, compared to the wild type heat-stable RecA protein. Further, preferably, the heat-stable RecA mutant protein of the present invention has a high homologous recombination activity, compared to the wild type heat-stable RecA protein. The wild type heat-stable RecA protein means that the amino acid sequence of the heat-stable RecA protein found in an extreme thermophile that has been isolated from nature and the base sequence encoding that the heat-stable RecA protein do not have mutation sites in which intentional or unintentional mutations have occurred.

The wild type heat-stable RecA protein, which serves as a basis of the heat-stable RecA mutant protein, is derived from an extreme thermophile. Specifically, RecA proteins derived from *Thermus, Thermococcus, Pyrococcus*, or *Thermotoga* are suitable examples for using as an extreme thermophile RecA protein in the present invention. Preferably, RecA proteins derived from *Thermus thermophilus* or *Thermus aquaticus* is used. However, the wild type heat-stable RecA protein is not limited to these examples.

Here, the "function for contributing to an increase in an amplification specificity in the nucleic acid amplification reaction" means that, in a nucleic amplification reaction, non-specific amplification that is not related with the template nucleic acid is hardly observed, and it is possible to amplify the template nucleic acid with high yield. Preferably, this also means a function that can increase the template nucleic acid amplification specificity by a factor of 2 to 4. For example, this means that the function is substantially identical to the function of the protein of the present invention with the amino acid sequence set forth in Sequence Number 2, which is able to contribute to improvement of the template nucleic acid amplification specificity. The protein of the present invention is referred to as Hyper-TthRecA in the examples. Also, preferably, the nucleic acid amplification reaction indicates PCR using a thermostable DNA polymerase. However, this does not mean that other nucleic acid amplification methods using different enzymes are not used. Therefore, the nucleic acid amplification reaction includes known techniques such as ligase chain reaction (hereinafter, the reaction may refer to as LCR), strand displacement amplification reaction (hereinafter, the reaction may be refer as to SDA), Rolling cycle amplification reaction (hereinafter, the reaction may be refer as to RCA).

Specifically, the heat-stable RecA mutant protein has a mutation site in which mutation involving deletion or substitution to at least one or more specific amino acids occurs in an amino acid sequence composing an acid region at C-terminal end of the wild type heat-stable RecA protein. Here, the "mutation involving deletion or substitution to at least one or more specific amino acids" means mutation involving deletion or substation of such a number of amino acids that can be deleted from or substituted for the gene encoding the protein serving as the basis of mutation, by application of a known technique such as DNA recombination, point mutation, etc or combination thereof. Such mutation can be induced artificially or can occur unintentionally in nature. The heat-stable RecA mutant protein of the present invention includes both types of mutations.

Here, the acid region means a region which is rich in acidic amino acids and exists at the C-terminal end in the wild type heat-stable RecA protein. Specifically, a region which is composed of 1 to 16 amino acids from the C-terminal end of the wild type heat-stable RecA protein are considered as the acid region.

It is preferable that the heat-stable RecA mutant protein of the present invention has mutation sites in the amino acid sequence composing the acid region so as to increase the PI (isoelectric point) value, compared to the wild type heat-stable RecA protein. For example, in a RecA protein derived from *Thermus thermophilus* which is described circumstantially in the examples, the acid region exists at the C-terminal end. Every time the amino acid at the C-terminal end is deleted, the PI value increases. [Wild type (1~340 amino acid): 5.33, Mutant (1~339): 5.46, Mutant (1~337): 5.64, Mutant (1~336): 5.90, Mutant (1~335): 6.31, Mutant (1~327): 7.60] As the heat-stable RecA mutant protein of the present invention, it is preferable to have such a mutation. In particular, it is preferable that the mutation occurs so as to increase the PI value more than 1. Therefore, it is preferable that the mutation such as deleting the acid region, deleting the acidic amino acids composing the acid region, or substituting for the amino acids with the one other than acidic amino acid occurs.

As described above, the heat-stable mutant RecA protein of the present invention is obtained by deletion, or substitution of the amino acids composing the acid region of the wild type heat-stable RecA protein. Preferably, the heat-stable RecA mutant protein is obtained by deleting or substituting 1 to 16 amino acids from the C-terminal end of the wild type heat-stable RecA protein. More preferably, the amino acid sequence composed of 1 to 16 amino acids from the C-terminal end is cut at an arbitrary position to be deleted. In particular, the protein in which 1 to 13 amino acids from the C-terminal end are deleted is considered as a preferable example.

Specifically, one illustrative example of the heat-stable mutant RecA protein of the present invention is one in which at least one of amino acids from 328th to 340th of Sequence Number 2, which indicates a RecA protein derived from *Thermus thermophilus*, is deleted or substituted. More preferably, the one in which 328th, 336th, 337th, 338th and 340th acidic amino acids of Sequence Number 2 are deleted or substituted with any amino acids other than acidic amino acid. In particular, it is preferable that, for example, a heat-stable RecA mutant protein is obtained by deleting 13 amino acids, from 328th to 340th, of Sequence Number 4, which indicates the wild type RecA protein derived from *Thermus thermophilus*. Sequence number 2 of the sequence listing shows the amino acid sequence of the above-described the wild type RecA protein and Sequence number 1 of the sequence listing shows a base sequence encoding the heat-stable RecA mutant protein.

The heat-stable mutant RecA protein of the present invention is obtained by a known method. For example, the mutation is performed on DNA which encodes the wild type heat-stable mutant RecA protein serving as the basis of the mutation and a host cell is genetically transformed by way of the mutant DNA which is obtained by the above-mentioned mutation. Then, the heat-stable mutant RecA protein is obtained by collecting it from a culture of the transformant.

DNA which encodes the wild type heat-stable mutant RecA protein serving as the basis of the mutation is obtained by way of a known gene cloning technique. For example, the DNA encoding the wild type heat-stable mutant RecA protein is obtained by designing a primer based on gene information obtained by searching known databases such as GenBank, and carrying out PCR with a genome DNA serving as a template. The genome DNA is extracted from an extreme thermophile which is able to produce RecA proteins. Based on known gene information, it is also possible to obtain the DNA by synthesizing by way of a nucleic acid biosynthesis method such as a phosphoramidite method which is a common technique.

Here, as sequence information of the heat-stable RecA protein serving as a preferable basis of the mutant protein of the present invention, sequence number 4 of the sequence listing shows the amino acid sequence of the wild type RecA protein derived from *Thermus thermophilus* and Sequence number 3 of the sequence listing shows the base sequence encoding the RecA mutant protein.

There is no limitation on the method for performing the mutation on the DNA encoding the heat-stable RecA protein. Mutagenesis techniques for generating mutant proteins, which are known to those skilled in the art, may be employed. For example, a known technique such as site directed mutagenesis technique, PCR mutagenesis technique which introduces mutations by way of PCR methods, or transposon-insertion mutagenesis technique may be employed. Also, commercial mutagenesis kits (For example, QuikChange (registered brand), Site-directed Mutagenesis Kit (Stratagene product)) may be employed. Once the amino acid sequence of the target heat-stable RecA mutant protein is determined, a proper base sequence encoding the amino acid sequence is determined. The DNA encoding the heat-stable RecA mutant protein of the present invention is synthesized by way of a nucleic acid synthesis technique such as phosphoramidite method which is a common technique or the like.

Specifically, the DNA is obtained by carrying out PCR in the condition that DNA encoding the wild type heat-stable RecA protein and oligonucleotide including the sequence, in which the desired mutation (deletion or substitution) is carried out, serve as a template and a primer, respectively. Also, the DNA encoding the deletion mutant is obtained by decomposing terminal DNA of the DNA encoding the wild type heat-stable RecA protein with exonuclease or the like.

In order to transform the host cell by way of the obtained mutant gene, a known expression host-vector system such as *E coli* may be employed. For example, the mutant gene is ligated into a DNA vector which is able to amplify stably the heat-stable RecA mutant protein and the DNA vector is transformed into *E. coli* which effectively expresses the heat-stable RecA mutant protein. Then, the *E. coli* is inoculated in a culture including a carbon source, a nitrogen source and other necessary nutrients and it is grown following the common procedure to express the heat-stable RecA mutant protein.

It should be noted that as long as the expression vector includes e.g. a promoter sequence and a sequence such as a multicloning site having at least one restriction enzyme site to which a gene encoding the heat-stable RecA protein can be inserted, and can express the protein in the host cell, then any expression vector can be used. As an example of a favorable promoter, it is preferable that the T7/lac is employed.

Further, the expression vector may include other known base sequences. There are no limitations on the known base sequences. Possible examples thereof include a stable leader sequence that gives stability to the expression product and a signal sequence that facilitates secretion of the expression product. The vector can include also a marking sequence that can give phenotype selectivity to a transformed host. Some non-limiting examples of such marking sequences are a neomycin-resistant gene, a kanamycin-resistant gene, a chloramphenicol-resistant gene, an ampicillin-resistant gene, and a hygromycin-resistant gene.

It is possible to employ a commercially available *E. coli* expression vector (such as the pET protein expression system: Novagen product) as this expression vector, and it is also possible to fabricate and use an expression vector that suitably incorporates the desired sequence.

The host cell is not limited to *E. coli*, and it is also possible to use *Bacillus bacteria, Pseudomonas* bacteria, or the like. Further, the host cell is not limited to prokaryotes and it is possible to use eukaryotic cell as well. For example, yeast such as *Saccharomyces cerevisiae*, insect cells such as Sf9 cells, or animal cells such as CHO cells or COS-7 cells, can be used favorably.

The extraction and purification of the heat-stable RecA mutant protein of the present invention from the culture of the transformant obtained by a method described above is carried out as described in FIG. 1. Briefly described, a cell containing *E. coli* is collected from the culture of the transformant. Then, the cell is suspended in the buffer solution and is crushed by an ultrasonic treatment to obtain an extract thereof. It is preferable to carry out the pulverization in the buffer solution properly including lysozyme or surface active agents. Subsequently, the supernatant is collected by centrifugal separation, filtration or the like and the protein derived from the transformant is inactivated by a thermal processing to obtain a crude extract of the heat-stable RecA mutant protein. Preferably, the thermal processing is carried out at 65° C. for 60 minutes. The crude extract is processed by hydrophobic chromatography, cation exchange cellulose chromatography, and cation exchange phosphoric cellulose chromatography. It is preferable to perform the processing sequentially in the above order, however, the order is not limited. At that time, it is preferable to carry out the hydrophobic chromatography in the presence of ammonium sulfate. Thus, the heat-stable RecA mutant protein of the present invention is purified from the transformant.

It is also possible to omit the cation exchange cellulose chromatography (FIG. 2). However, it is not possible to purify the heat-stable RecA mutant protein by other purification methods which are known in the literature. The binding capacity to the nucleic acid is mutated by the mutation of the acid region and it becomes difficult to separate the heat-stable RecA mutant protein from contaminants derived from the transformant, in particular, the nucleic acid components. Therefore, the production method of the heat-stable RecA mutant protein comprises a part of the present invention. Also, the production method of the present invention may be utilized for not only the heat-stable RecA mutant protein of the present invention, but for the purification of proteins, which are not easily separated from the contaminants derived from other transformants.

It is possible to confirm by way of a known amino acid analysis method that the purified protein is the heat-stable RecA mutant protein of the present invention having the mutation sites where the desired mutation occurs. For example, an automatic amino acid determination based on Edman sequencing may be employed. Further, it is also possible to confirm the result of the purified protein by measuring the homologous recombination activity of the RecA protein by a known method such as D-Loop formation assay and comparing the result with that of the wild type heat-stable protein, which does not have the mutation site. Also, it is possible to confirm the result of the purified protein by using the RecA protein in PCR for comparing it with the wild type heat-stable protein which does not have the mutation site and checking whether the specificity to the template nucleic acid has increased. For example, the checking is performed by methods disclosed in the examples 2 to 7 of the present invention.

As described above, the heat-stable RecA protein of the present invention is improved in terms of the ability for contributing to the increase in the amplification specificity of the target nucleic acid in the nucleic amplification reaction. Therefore, when the heat-stable RecA protein is applied to the nucleic amplification reaction, the nucleic acid amplification, which is specific to the target nucleic acid and is effective, is possible. Further, the non-specific amplification which is not related with the target nucleic acid is restrained. Thus, it is possible to carry out the nucleic amplification without receiving the influence of the background noise. Also the protein of the present invention improves enzymic activities of the DNA polymerase and the like and also improves the specificity of the nucleic acid amplification with the above-mentioned effect. As described above, the protein of the present invention can be broadly utilized in various industrial fields, in particular, molecular biology.

The heat-stable RecA mutant protein of the present invention facilitates homologous recombination. In experiments of gene recombination, effective gene introduction can be realized by the heat-stable RecA mutant protein. For example, the protein of the present invention can be employed in the gene introduction into embryonic stem cells for producing transgenic animals. Thus, the protein can be broadly utilized in the filed of molecular biology such as gene phenomenon analysis.

The present invention provides the nucleic acid amplification method of the template nucleic acid by using the heat-stable mutant RecA protein of the present invention. In the nucleic acid amplification method of the present invention, the heat-stable mutant RecA protein of the present invention is added to carry out the nucleic acid amplification reaction.

Here, the application of the heat-stable RecA mutant protein of the present invention to PCR is described. PCR is a method of amplifying DNA in a chain reaction with a thermostable DNA polymerase. The principle of PCR is that a nucleic acid for amplification (hereinafter, the acid may be abbreviated to target nucleic acid) is amplified by $2^n$ times by repeating three steps of temperature changes in n cycles in the presence of primers and the thermostable DNA polymerase.

More specifically, a PCR reactant mixture is prepared including the heat-stable RecA mutant protein of the present invention, a target nucleic acid, a thermostable DNA polymerase, primers, dNTP and an appropriate buffer. The PCR reactant mixture is subject to temperature cycles consisting of heat denaturation, annealing, and extension reaction to carry out PCR. The reactant mixture may be prepared including nucleoside 5'-triphosphate (hereinafter, referred to as NTP) as well as dNTP. If necessary, the primers and dNTP may be labeled by appropriate labeling materials for detection. The labeling materials are known and those skilled in the art may select suitable one.

The target nucleic acid for amplification in the present invention is not limited in its origin, length, and base sequence. The target nucleic acid may be any one of either single-stranded or double-stranded nucleic acids. Specifically, it may be a genome DNA of an organism, or a fragment which is cleaved from the genome DNA by physical means or restriction enzyme digestion. Furthermore, a DNA fragment which is inserted into a plasmid, a phage or the like can be suitably used. Furthermore, the target nucleic acid may be one that is prepared or isolated from a sample which possibly contains a nucleic acid. In addition, it may be any target nucleic acid such as artificial products such as a DNA fragment synthesized with a DNA automatic synthesizer which is commonly used in the related technical field, and a cDNA fragment synthesized with mRNA as a template.

A primer is a sequence which is designed to be complementary to a specific sequence of a target nucleic acid. Particularly, it has preferably a base sequence complementary to both ends of the target sequence to be amplified. For the simplest system, two primers are required, but when multiplex PCR or the like is carried out, three or more primers may be used. Furthermore, only one primer may be used suitably for the amplification reaction. Design of the primer is determined by searching the sequence of the target nucleic acid in advance, except that a random primer is used. Also, in searching the base sequence of the target nucleic acid, database such as GeneBank and EBI can suitably used.

A primer may be prepared by a chemical synthesis based on the phosphoamidite method and the like, and when the nucleic acid to be targeted has been already acquired, its restriction enzyme fragment or the like can be used. When preparing the primer based on the chemical synthesis, it is designed based on sequence information of the target nucleic acid before synthesis. After the synthesis, the primer is purified by means such as HPLC. Furthermore, when carrying out the chemical synthesis, a commercially available automatic synthesizer can be also used. Here, the term complementary means that the primer and the target nucleic acid can specifically bind to each other according to the base-paring rule, and form a stable double-stranded structure. It encompasses not only complete complementarity, but also partial complementarity, which has only some nucleic acid bases suitably paired according to the base pairing rule as long as the primer and the target nucleic acid can sufficiently form a stable double-stranded structure. The number of the bases should be large enough to recognize specifically the target nucleic acid, but conversely, if it is too large, it is not preferable since it may induce a non-specific reaction. Therefore, a suitable length is determined depending on many factors such as the sequence information of the target nucleic acid such as GC content, and hybridization reaction conditions in the reaction conditions such as reaction temperature and salt concentration in the reaction solution, but it is preferably 20 to 50 bases in length.

Here, the thermostable DNA polymerase to be used is not particularly limited as long as it is a thermostable DNA polymerase which can be usually used in PCR. For example, it includes a DNA polymerase derived from thermophilic bacteria such as a Taq polymerase derived from *Thermus aquaticus*, a Tth polymerase derived from *Thermus thermophilius*, a Bst polymerase derived from *Bacillus Stearothermophilus*, Vent DNA polymerase derived from *Thermococcus litoralis*, KOD DNA polymerase derived from *Thermococcus Kodakara*, and a Pfu polymerase derived from *Pyrococcus furiousu* and the like.

For dNTP, four kinds of deoxynucleotide corresponding to each base of adenine, thymine, guanine and cytosine, are used. Particularly, a mixture of dGTP, dATP, dTTP and dCTP is preferably used. Furthermore, a derivative of deoxynucleotide may be also included as long as it can be incorporated by a thermostable DNA polymerase into a DNA molecule which is synthesized and extended in PCR. Such derivative is, for example, 7-deaza-dGTP, 7-deaza-dATP and the like, which can be used, for example, by replacing dGTP or dATP with them, or in the presence of both of them. Therefore, as long as four kinds are included corresponding to each base of adenine, thymine, guanine and cytosine which are necessary for nucleic acid synthesis, use of any derivative is not excluded.

The buffer solution is generally prepared by containing suitable buffer components, magnesium salts and the like. As the buffer components, Tris acetic acid, Tris-HCl, and a phosphate salt such as sodium phosphate and calcium phosphate can be suitably used, and particularly, Tris acetic acid is preferably used. The final concentration of the buffer components is adjusted in the range of 5 mM to 100 mM. Furthermore, pH of the buffer solution is adjusted preferably in the range of 6.0 to 9.5, more preferably 7.0 to 8.0. Furthermore, pH of the buffer is adjusted preferably in the range of 6.0 to 9.5, more preferably 7.0 to 8.0. Furthermore, the magnesium salt is not particularly limited, but magnesium chloride, magnesium acetate and the like can be suitably used, and magnesium acetate is particularly preferable. Furthermore, if necessary, it is possible to add a potassium salt such as KCL and the like, DMSO, glycerol, betaine, gelatin, Triton and the like. In addition, it is possible to use a buffer solution which is accompanied in the commercially available thermostable DNA polymerase for PCR. The composition of the buffer solution can be suitably varied depending on the kind of the DNA polymerase to be used, or the like. Particularly, it can be suitably set, taking into consideration of the influence on the ionic strength of compounds such as $MgCl_2$, KCl and the like, the various additives such as DMSO, glycerol and the like that may affect the melting point of DNA, and the concentration of the additives.

The reaction solution is preferably prepared in a volume of 100 μl or less, particularly in the range of 10 to 50 For the concentration of each component, the heat-stable RecA mutant protein of the present invention is preferably used to be contained with the concentration of 0.004 to 0.02 μg/μl in the reaction system. Concentration of the components other than the heat-stable RecA mutant protein of the present invention can be suitably set by those skilled in the art since PCR is known. However, as confirmed in the examples 4 to 6 which will be described below, it is possible to reduce the amounts of the DNA polymerase and the primer by adding the heat-stable RecA mutant protein of the present invention. Thus, the reaction solution can be prepared so as to reduce the amounts of the DNA polymerase and the primer, compared to the consumed amount of the known PCR. For instance, the reaction solution may be prepared by half to quarter of the original amounts of the DNA polymerase and the primer. For example, the target nucleic acid is preferably prepared in a concentration of 10 pg to 1 μg per 100 μl, and the primer DNA is preferably prepared in a final concentration of 0.01 to 10 μM, particularly 0.1 to 1 μM. Furthermore, the thermostable DNA polymerase is preferably used in a concentration of 0.1 to 50 Units, particularly 1 to 5 Units per 100 μl. And, dNTP is preferably prepared in a final concentration of 0.1 mM to 1M. In addition, the magnesium salt is preferably prepared in a final concentration of 0.1 to 50 mM, particularly 1 to 5 mM. PCR is carried out according to the following steps, and these steps are carried out in the presence of the heat-stable RecA mutant protein of the present invention.

(1) Thermal denaturation of template nucleic acid
(2) Annealing of primer
(3) Extension reaction by thermostable polymerase By repeating suitable times the reaction consisting of the three step temperature change of the above-mentioned (1) to (3) as one cycle, synthesis of the other nucleic acid chain having complementation is initiated with the primer as a starting point and the target nucleic acid as a template. As a result, the target nucleic acid is amplified by $2^n$ times with the reactions of n cycles. The thermocycle number is determined depending on the kind, amount, purity and the like of the target nucleic acid as a template, but preferably 20 to 40 cycles, particularly 32 to 36 cycles from a view point of the efficient nucleic acid amplification and restraint of the non-specific amplification.

Each step will be illustrated below.

(1) Thermal Denaturation of Template Nucleic Acid

A double-stranded nucleic acid is denatured and dissociated to single-stranded one by heating. Preferably, it is carried out at 92 to 98° C. for 10 to 60 seconds. In addition, in the case where a long DNA region is amplified, only the first thermal denaturation can be set to a low temperature (for example, at 92° C. or so) in order to prevent dissociation of the template DNA.

(2) Annealing of Primer

By lowering the temperature, a hybrid is formed between the template nucleic acid which has been thermally denatured and becomes single-stranded one in the above-mentioned (1), and the primer. The annealing is preferably carried out for 30 to 60 seconds. In addition, the annealing temperature is preferably set as Tm (melting point) of the oligonucleotide used as the primer after estimating the Tm. It is known that when the high annealing temperature is high, the binding capacity of the primers which are template specific improves, however, the primers do not bind to the template nucleic acids when the annealing temperature is too high. Normally, the annealing temperature is set to 50 to 70° C., however, it is possible to apply the higher annealing temperature by adding the heat-stable RecA mutant protein (see example 7). For example, it is possible to apply a PCR condition in which the annealing temperature is set so as to plus 5 degree to the normal cases. Therefore, it is possible to carry out the nucleic acid amplification more specifically.

(3) Extension Reaction by Thermostable Polymerase

An extension reaction of a nucleic acid strand at a primer is carried out by a thermostable polymerase at the 3' end. The extension reaction temperature is suitably set depending on the kind of the thermostable polymerase, and the reaction is preferably carried out at 65 to 75° C. In addition, when the target sequence is 1 kb or less, the extension time is sufficient with about 1 minute. When the target sequence is more than the above range, it is preferably elongated at a rate of 1 minute per 1 kb.

The general PCR method, which is a nucleic acid amplification of the present invention, will be described above. The nucleic acid amplification of the present invention will be applied to variations of PCR such as adapters addition PCR, mutant allele specific amplification (MASA), asymmetric PCR, inverse PCR (IPCR), reverse transcription-PCR (RT-PCR), single strand conformational polymorphism PCR (PCR-SSCP method), arbitrarily primed PCR (AP-PCR), RACE, multiplex PCR and the like. However, the application of the nucleic acid amplification of the present invention is not limited to those examples, and it is possible to apply the nucleic acid amplification to all types of PCR variations.

Thus, it is possible to perform the nucleic acid amplification, which is specific to the target nucleic acid and is effective, by carrying out the nucleic amplification reaction in the presence of the heat-stable RecA mutant protein of the present invention. The non-specific amplification which is not related to the target nucleic acid is restrained. Therefore, it is possible to carry out the nucleic acid amplification without receiving the influence of the background noise. Namely, it is possible to maintain the condition that sequence specificity in the primer for the target nucleic acid serving as a temple is improved. As a result, the non-specific amplification due to false priming such as annealing the primer to sites other than the target sequence or annealing between primers is restrained. Thus, it is possible to realize the nucleic acid amplification with the higher specificity. Also, the heat-stable RecA mutant protein of the present invention has the improved ability for contributing to the increase in the amplification specificity of the target nucleic acid in the nucleic acid amplification reaction and further improves the enzymatic activities of the DNA polymerase and the like. For the reason, according to the nucleic amplification of the present invention, the consumed amount of the thermostable DNA polymerase is reduced, and thus it is possible to provide inexpensive nucleic acid amplification. Further, the annealing temperature can be set at a higher temperature in the nucleic acid amplification reaction. Thus, it is possible to carry out the nucleic acid amplification which is more specific to the target nucleic acid. Also, since the heat-stable RecA mutant protein of the present invention is a heat-stable enzyme, it is possible to continually achieve the above-mentioned effect. As a result, it is possible to achieve the nucleic acid amplification with the high specificity through all cycles of the nucleic acid amplification reaction including heat processing.

Also, the present invention provides a nucleic acid amplification kit for amplifying the nucleic acid. The nucleic acid amplification kit of the present invention comprises a DNA polymerase and the heat-stable RecA mutant protein. Further, the kit may properly contain necessary components for PCR such as suitable buffers, magnesium salt, dNTP and the likes. If the kit is used for detecting pathogens using a desired nucleic acid, the kit may contain any primer which is specific to the desired nucleic acid amplification and the like. As described above, by comprising such components necessary for PCR amplification as a kit, simple and prompt PCR amplification is possible.

The heat-stable RecA mutant protein of the present invention, and the kit and the nucleic acid amplification using the protein may be utilized in various field such as medical, biological chemistry, environmental fields, and food industry. For instance, the protein, and the kit and the nucleic acid amplification using the protein may be utilized when a large quantity of DNA is prepared from a small amount of a sample for a genotypic analysis, or when DNA is prepared for a DNA sequence. Furthermore, the protein and the kit and the technique using it is utilized when DNA used for a DNA chip is prepared from a small amount of a sample extracted from an animal or a plant cell, microorganisms, or the like. Thus, it is applicable to a variety of utilizations.

Specifically, the medical field, gene diagnosis as detection of single nucleotide polymorphism, and detection of pathogenic agent such as SARS, influenza and other viruses, and bacterium are cited as examples. In particular, the present invention is preferably applied to the detection method of the single nucleotide polymorphism. It is possible to restrain non-specific binding and effectively restrain the false priming of the primers. The primer binding a nucleic acid other than the target nucleic acid and that the primers binding each other are considered as examples of the non-specific binding. Therefore, a primer which is complementary to a nucleic acid having a desired single nucleotide polymorphism is used, and thus it is possible to effectively amplify the nucleic acid having the single nucleotide polymorphism. On the other hand, nucleic acids which do not have the single nucleotide polymorphism are not amplified or the amplification of the nucleic acids is not restrained. Consequently, it is possible to specifically amplify the nucleic acid having the single nucleotide polymorphism. Further, the effectiveness is intensified by high annealing temperature which is achieved by the present invention and thus it is possible to effectively detect the single nucleotide polymorphism with high sensitivity. In biological chemistry, identification of an individuals and identification of organism species are cited as examples of the application of the present invention.

In environmental field, environmental measurement such as pathogen detection of viruses and bacterium in the environment and searching of new effective microorganisms are cited as examples of the application. Further, in the food industry, determination of inclusion of gene recombination crops and screening of fake brand-name foods are cited as examples of the application. However, the application is not limited to the examples. The method of the present invention is applicable to any utilization to which the nucleic acid amplification technique is applicable.

Another Example

1. The heat-stable RecA mutant protein is applied to concentration or isolation of a target cDNA clone from the DNA library. More specifically, the heat-stable RecA mutant protein of the present invention is applied when PCR is carried out under the following condition: a part of the target cDNA sequence to be concentrated or isolated is used as a primer and the DNA library is used as a template. Herein, PCR and other known nucleic acid amplification methods may be employed. Thus, it is possible to restrain the non-specific amplification which is not related with the target cDNA and to specifically amplify only the target cDNA. Therefore, it is possible to specifically and effectively concentrate or isolate the desired target cDNA clone by applying the heat-stable RecA mutant protein to the cloning of the target DNA clone from the DNA library. Specific and effective cDNA cloning may greatly contribute to analyses of gene expression, occurrence, differentiation and the like and to production of useful compounds.

A DNA library which contains the target DNA region desiring the concentration or the isolation or a DNA library which is expected to contain the target DNA region is employed. The DNA library is a genome library or a cDNA library. However, in particular, the cDNA library is preferable. The genome library as used herein is used as a concept indicating a DNA aggregate which is cloned. In the cloned DNA aggregate, total genome DNA of a specific organism is randomly incorporated into a vector. On the other hand, the cDNA library is used as a concept indicating an aggregate of cDNA fragments created by synthesizing cDNA by reverse transcription reacting the mRNA of a specific tissue, a cell, or an organism and incorporating it into a vector.

Generally, a primer is designed to be complementary to a specific sequence of the target nucleic acid. Particularly, it is preferable that the primers have base sequences which are complementary to both ends of the target sequence to be amplified and a partial sequence of the target cDNA to be concentrated or isolated is preferably employed. The design of primers is a known technique. Primers are designed based on the base sequence of the targeted cDNA and are prepared by known techniques such as chemical synthesis.

2. The heat-stable RecA mutant protein of the present invention is applied to reverse transcription from RNA to DNA. Specifically, the heat-stable RecA mutant protein of the present invention is applied when cDNA is synthesized from RNA by the reverse transcription using a random hexamer primer, an oligo-dT hexamer primer, and a target gene specific primer in the presence of reverse transcriptase enzyme. Further, the heat-stable RecA mutant protein of the present invention is applied when the amplification reaction is carried out with the synthesized cDNA serving as a template. As the amplification reaction, it is possible to employ known nucleic acid techniques as well as PCR. The synthesis of the non-specific cDNA, which is not related with the target RNA, is restrained by applying the present invention and thus it is possible to synthesize cDNA specifically for the target RNA. Therefore, the application of the heat-stable RecA mutant protein of the present invention to the reverse transcription system allows the cDNA to synthesize efficiently and specifically for the target RNA. Conversion from RNA to cDNA is an essential method in gene engineering and the application is utilized in detection of gene expression and quantitation thereof, RNA structural analysis, cDNA cloning and so on. Thus, the application has a high potential in the field.

There is no limitation on RNA used herein. mRNA, tRNA, rRNA and the likes as well as total RNA can be used. RNA is prepared from cells and tissues, where the desired genes express or are expected to express, using a known technique. For example, guanidine/caesium TFA method, lithium chloride/urea method, AGPC method and the likes are employed. Also, there is no limitation on primers. Any primers can be employed as far as the primer can anneal to the template RNA in the reaction condition where the primer is applied. As described, the random hexamer primer, the oligo-dT hexamer primer, and the target gene specific primer can be employed. The target gene specific primer used herein has base sequences which are complementary to a specific template RNA, and it is preferable to employ 3' primer which is used in general PCR amplification system.

Hereinafter, examples will be described below, and the present invention will be illustrated in more detail. However, the present invention is not limited thereto.

In the examples described below, a heat-stable RecA protein derived from *Thermus thermophilus* is used as an example of the heat-stable RecA protein (hereinafter, the protein may be referred to as TthRecA protein). However, the heat-stable RecA protein is not limited to the example.

Example 1

Preparation of the TthRecA Mutant Protein

A TthRecA mutant protein in which acidic amino residues were deleted at the C-terminal end of the wild type TthRecA protein.

(Method)
(1) Gene Cloning

The TthRecA mutant protein (referred to as Hyper-TthRecA protein, hereinafter), in which 13 acidic amino residues at the C-terminal end of a wild type TthRecA protein were deleted, was constructed. The design of the Hyper-Tth RecA protein is shown in FIG. 3. Firstly, the cloning of the gene which encodes the Hyper-Tth RecA protein was carried out. Below-described two oligonucleotide primers were synthesized based on known sequence information (Gen Bank: ACCESSION UO3058) of the wild type TthRecA protein. These primers are designed for deleting 13 acidic amino acid residues at the C-terminal end of the wild type Tth RecA protein.

Primer 1
5'-gctcatatggacgagagcaagcgcaa-3'
(SEQ ID No. 5)
Primer 2
5'-cgcaagcttagcccgcggccaggacca-3'
(SEQ ID No. 6)
(refer to GenBank:ACCESSION UO3058: *Thermus thermophilus* RecA protein (recA) gene)

Next, PCR was carried out using the above-mentioned primers 1 and 2 with *Thermus thermophilus* HB8 genomic DNA (Takara-Bio product) serving as a template. The PCR reactant mixture (50 µl) was prepared by mixing 50 ng of the template DNA, 0.6 µM (final concentration) of each primer 1 and 2, 1.25 unit of a DNA polymerase, 0.2 mM (final concentration) of a dNTP mixture with 1×PCR buffer (takara-Bio product). ExTaq-HS DNA polymerase (takara-Bio product) was used as the DNA polymerase. The PCR reactant mixture was subject to 1 cycle of the final reaction (1 cycle: for 3 minutes at 72° C.) after 35 cycles of the amplification reaction (1 cycle: for 10 seconds at 98° C., for 30 seconds at 55° C., and for 60 seconds at 72° C.).

The obtained amplification products were cleaved with restriction enzymes Nde-I and Hind-III after the purification. The obtained DNA fragment was ligated into an expression vector pET22b (Novagen product) which was cleaved with restriction enzymes Nde-I and Hind-III. Then, the vector was transformed to *E. coli* BL21 (DE3) pLysS (Takara-Bio product) to obtain Hyper-TthRecA expressing clones. Sequence determination was carried out to confirm if the expressing clones of interest were obtained. A cycle sequence reaction was carried out using BigDye terminator (Applied Biosystems product) with the expressing clone, which was obtained in the above-described process, serving as a template. At this time, T7 promoter sequence and T7 terminator sequence were used as the primers and the sequence was determined by using a sequencer (ABI 3130, Applied Biosystems product) following protocols described by the manufacturer. The result confirmed that the gene encoding the Hyper-TthRecA protein of interest was cloned.

(2) Expression and Purification of the Protein

The Hyper-TthRecA expressing clone, which was obtained in the above-described procedure, was cultivated at 37° C. in a LB liquid medium including 100 µg/ml of ampicillin until the condition reaches $OD_{600}$=0.6. Further, 1 mM of IPTG was added thereto and the Hyper-TthRecA expressing clone was cultivated for 4 hours. At this time, the cultivation was carried out following a general cultivation method of *E. coli*.

After the cultivation, the purification of the Hyper-TthRecA protein was conducted based on a method described in FIG. 1. The 50 g of the cell which was collected and frozen was added to 200 ml of TS buffer, lysozyme (final concentration 0.5 mg/ml), polyoxyethylene cetyl ether surfactant (Brij 58: final concentration 0.4%) on the ice. Then, the cell was crushed by an ultrasonic treatment and the crushing process liquid of the cell was obtained. The ultrasonic treatment was performed 3 to 5 times a minute on the ice. ETDA (final concentration 5 mM) and KCl (final concentration 1 mM)

were added to the crushing process liquid of the cell so as to make the total amount 280 ml. Next, the supernatant was collected by centrifugation at 60,000×g for 60 minutes at 4° C. and was subject to a thermal processing at 65° C. for 60 minutes. After the thermal processing, the supernatant was collected by centrifugation at 60,000×g for 20 minutes. Ammonium sulfa was added to the supernatant so that the final concentration was 0.8M and the solution was applied to hydrophobic chromatography column (Butyl Toyopearl: 650M: TOSO product) which was equilibrated with 200 ml of a TEM 0.8 AS buffer. After washing the column with 300 ml of the PEM 0.8 AS buffer, the protein was eluted with 200 ml of a PEM buffer and all peaks were collected. Subsequently, the collected fractions were dialyzed twice using the PEM buffer to be applied to cation exchange cellulose chromatography column (CM52: Whatman) which was equilibrated with 300 ml of the PEM buffer. The column was washed with 450 ml of a PEM 0.3 K buffer and the protein was eluted with 300 ml of a PEMK buffer to collect all peaks. The collected fractions were dialyzed for 20 hours with the PEM buffer and the solution was subject to cation exchange cellulose phosphate chromatography column (P11: Whatman product) which was equilibrated with 300 ml of the PEM buffer. The column was washed with 450 ml of the PEM buffer and the protein was eluted with 300 ml of the PEMK buffer to collect all peaks. Then, the collected fraction was dialyzed with TEDG buffer for 20 hours at 4° C. to obtain the Hyper-TthRecA protein. The Hyper-Tth RecA protein was stored at −20° C. for a next experiment.

The compositions of the buffers used herein are shown below.

| Buffer | Composition |
| --- | --- |
| TS buffer | 25 mM Tris (pH 8.0), 25% saccharose |
| TEM 0.8 AS buffer | 25 mM Tris (pH 7.5), 1 mM EDTA, 5 mM b-SH, 0.8 M AS |
| PEM 0.8 AS buffer | 25 mM $K_1K_2P0_3$ (pH 6.5), 1 mM EDTA, 5 mM b-SH, 0.8 M AS |
| PEM buffer | 25 mM $K_1K_2P0_3$ (pH 6.5), 1 mM EDTA, 5 mM b-SH |
| PEM 0.3 K buffer | 25 mM $K_1K_2P0_3$ (pH 6.5), 1 mM EDTA, 5 mM b-SH, 0.3 M KCl |
| PEMK buffer | 25 mM $K_1K_2P0_3$ (pH 6.5), 1 mM EDTA, 5 mM b-SH, 1 M KCl |
| TEDG buffer | 25 mM Tris (pH 7.5), 1 mM EDTA, 0.1 mM DTT, 60% glycerol | b-SH . . . 2-mercaptoethanol, AS . . . ammonium sulfate

Although details are not described here, the Hyper-TthRecA protein was purified even if the purification by cation exchange cellulose chromatography was omitted (FIG. 2). However, in this case, the yield decreased. On the other hand, the protein of the present invention was not purified by a method described in "Biocheistory" by Masui R et al., (Oct. 20, 1998, volume 37, 42th issue, Page 14788 to 14797 etc.).

Example 2

Confirmation of the Nature of the Hyper-TthRecA Protein

An experiment was conducted to evaluate the effect that the Hyper-TthRecA protein obtained in the example 1 has on PCR accuracy by comparing it with the case of the wild type TthRecA. Specifically, the experiment was conducted by comparing the amounts of the amplification products in PCR.

(Method)

The PCR reactant mixture (25 μl) was prepared by mixing 25 ng of a human genome DNA serving as a template DNA, 0.4 μg of the Hyper-TthRecA protein [Storage buffer: 50 mM Tris-HCl (pH7.5), 1.0 mM EDTA, 0.5 mM DTT, 50% w/v Glycerol], 0.8 μM (final concentration) of each primer, 2.0 unit of a DNA polymerase, and 0.2 mM (final concentration) of a dNTP mixture with 10 mM Tris-HCl Buffer (pH8.3), 50 mM KCl, and 1.5 mM $MgCl_2$.

In the example, "Human Genomic DNA" purchased from Promega was used as the human genome DNA and rTaq DNA polymerase (Takara-Bio product) was used as the DNA polymerase.

The below 4 kinds of primer sets were respectively used as the primers for preparing the PCR reactant mixtures.
Primer set A
  Primer 3
    5'-acaatgggctcactcaccc-3' (SEQ ID No. 7)
  Primer 4
    5'-ctaagaccaatggatagctg-3' (SEQ ID No. 8)
Primer set B
  Primer 5
    5'-gctcagcatggtggtggcataa-3' (SEQ ID No. 9)
  Primer 6
    5'-cctcataccttcccccccattt-3' (SEQ ID No. 10)
Primer set C
  Primer 7
    5'-gactactctagcgactgtccatctc-3' (SEQ ID No. 11)
  Primer 8
    5'-gacagccaccagatccaatc-3' (SEQ ID No. 12)
Primer set D
  Primer 9
    5'-aacctcacaaccttggctga-3' (SEQ ID No. 13)
  Primer 10
    5'-ttcacaacttaagatttggc-3' (SEQ ID No. 14)

Each PCR reactant mixture prepared as described above was subject to PCR in the same condition to obtain the amplification products. PCR is carried out through the following steps: (1) the thermal denaturation conducted at 92° C. for 30 seconds, (2) 35 cycles of the amplification reaction (1 cycle: for 10 seconds at 94° C., for 30 seconds at 55° C., for 60 seconds at 68° C.), and (3) 1 cycle of the final reaction (1 cycle: for 3 minutes at 68° C.).

After the amplification, an electrophoresis loading buffer was added to each amplification reactant to be stirred. Half of the solution was taken and was subject to 1.2% agarose gel electrophoresis. After the electrophoresis, the gel was stained with ethidium bromide to visualize DNA bands.

Instead of the Hyper-TthRecA protein, the wild type TthRecA protein [Storage buffer: 1.5 M KCl, 50 mM Tris-HCl (pH7.5), 1.0 mM EDTA, 0.5 mM DTT] was added to the PCR reactant mixture and the reactant mixture was subject to PCR carried out in the same procedure and the electrophoresis. The wild type TthRecA protein was prepared by the inventors of the present invention referring to a description in "Characterization of the oligomeric states of RecA protein: monomeric RecA protein can form a nucleoprotein filament, Biochemistry" by Masui R, Mikawa T, Kato R, Kuramitsu S (Oct. 20, 1998, volume 37, 42nd issue, Page 14788 to 14797).

Samples in which the experiment was preformed as described above without adding any Hyper-Tth RecA protein and any wild type Tth RecA Protein were produced. After carrying out PCR in the same procedure as described above, the samples were subject to electrophoresis and were used as controls.

(Result)

The results are shown in FIG. 4.

In FIG. 4, lanes 1 to 4 are the controls. These show the results of the amplification using the respective primer sets A, B, C and D.

In FIG. 4, lanes 5 to 8 show the results of the amplification carried out using the respective primer sets A, B, C and D in the presence of the wild type Tth RecA protein.

In FIG. 4, lanes 9 to 12 show the results of the amplification carried out using the respective primer sets A, B, C and D in the presence of the Hyper-TthRecA protein.

From the results of FIG. 4, in case that PCR was carried out with the Hyper-TthRecA added, the amplification products were observed in all of the primer sets examined in the experiment (Lanes 9 to 12). On the other hand, in case that PCR was carried out with the wild type TthRecA protein added and the cases of the controls, the amplification products were not observed for the primer set B (lanes 2 and 6). From these results, it was found that the addition of the Hyper-Tth RecA allows the amplification specificity of the template nucleic acid to improve, that is, the PCR accuracy is improved.

Example 3

Confirmation of the Nature of the Hyper-Tth RecA Protein—2

An experiment was conducted to evaluate homologous recombination activity of the Hyper-TthRecA protein obtained in the example 1 by comparing it with the wild type Tth RecA protein by way of D-Loop formation reaction.

(Method)

pBR322 DNA (Takara-Bio product) serving as a double-stranded target DNA and 150-mer of oligonucleotide (5'_tgt-tgtgcaaaaaagcggttagctccttcg-gtcctccgatcgttgtcagaagtaagttggccgcagtgttatcactcatggttatggc agcactgcataattctcttactgtcat-gccatccgtaagatgcttttctgtgactggtgagt? 3': SEQ ID No. 15) having a partial sequence thereof were used. 200 ng of the target DNA, 1 μmol of the respective labeled oligonucleotide 1 and 2, 3.0 μg of the Hyper-TthRecA protein, 4.8 mM of ATP-γS were incubated at 37° C. for 0~90 minutes in 30 mM of Tris acetate (pH7.2) and 20 mM of magnesium acetate. After the reaction, a protein extraction process was performed by adding 0.5% (W/Vol) of SDS and 0.7 mg/ml of Proteinase K thereto and incubating it at 37° C. for 30 minutes. Half of the solution was subject to 1% agarose gel electrophoresis. After the electrophoresis, the gel was stained with ethidium bromide to visualize DNA bands, and the formation of D-Loop was confirmed.

As for the wild type Tth RecA protein, the formation of D-loop was confirmed by the same procedure as described above.

The activity measurement was performed in the similar manner to described above for a RecA protein (purchased from Reche Diagnostics) derived from *E. coli*, not extreme thermophile and the samples were used as controls.

(Result)

The results are shown in FIG. 5. Bands of D-Loop products are indicated by arrows. In FIG. 5, lanes 1 to 7 show the results of the controls and the homologous recombination activity of the RecA protein, which is not derived from extreme thermophile, were confirmed by way of the D-Loop formation reaction for 0, 5, 10, 15, 30, 60, and 90 minutes. In FIG. 5, lanes 8 to 14 were used for confirming the homologous recombination activity of the wild type TthRecA protein by way of the D-Loop formation reaction for 0, 5, 10, 15, 30, 60, and 90 minutes.

In FIG. 5, lanes 15 to 21 were used for confirming the homologous recombination activity of the Hyper-Tth RecA protein by way of the D-Loop formation reaction for 0, 5, 10, 15, 30, 60, and 90 minutes.

From the results of FIG. 5, a larger amount of the D-Loop formation was observed in the Hyper-Tth RecA protein, compared to the wild type Tth RecA protein and the controls (comparison between lanes 15 to 20 and lanes 1 to 14). From those results, it was found that the Hyper-TthRecA protein had a higher homologous recombination activity, compared to the wild type TthRecA protein.

Example 4

Confirmation of the Nature of the Hyper-Tth RecA Protein—3

An experiment was conducted to evaluate the effect of the Hyper-TthRecA protein obtained in the example 1 on a DNA polymerase in PCR by comparing it with the wild type Tth RecA. In the example, a DNA polymerase derived from *Thermus aquaticus* was evaluated.

(Method)

The experiment was conducted by carrying out PCR using rTaq DNA polymerase (Takara-Bio product), which is a DNA polymerase derived from *Thermus aquaticus* of each concentration: 2.0, 1.0, 0.5, 0.25, and 0.13 unit. Specifically, the PCR reactant mixture (25 μl) was prepared by mixing 25 ng of a human genome DNA serving as a template DNA, 0.4 μg of the Hyper-TthRecA protein, 0.8 μM (final concentration) of each primer, one of rTaq DNA polymerase (Takara-Bio product) prepared to 2.0, 1.0, 0.5, 0.25, and 0.13 unit and 0.2 mM of a dNTP mixture with 10 mM Tris-HCl Buffer (pH8.3), 50 mM KCl, and 1.5 mM $MgCl_2$. The same human genome DNA was used as in the example 2.

As the primers, the primer set A (primers 3,4: SEQ ID No. 7,8) used in the examples 2 and 4 were also used to prepare the PCR reactant mixtures.

Primer set A

Primer 3

5'-acaatgggctcactcaccc-3' (SEQ ID No. 7)

Primer 4

5'-ctaagaccaatggatagctg-3' (SEQ ID No. 8)

Each PCR reactant mixture which was prepared as described above was subject to PCR to obtain the amplification productions. PCR was carried out through the following steps: (1) the thermal denaturation conducted at 92° C. for 30 seconds, (2) 35 cycles of the amplification reaction (1 cycle: for 10 seconds at 94° C., for 30 seconds at 55° C., for 60 seconds at 68° C.), (3) 1 cycle of the final reaction (1 cycle: for 3 minutes at 68° C.).

After the amplification, an electrophoresis loading buffer was added to each amplification reactant to be stirred. Half of the solution was taken and was subject to 1.2% agars gel electrophoresis. After the electrophoresis, the gel was stained with ethidium bromide to visualize DNA bands.

Instead of the Hyper-TthRecA protein, the wild type TthRecA protein was added to the PCR reactant mixture, and the reactant mixture was subject to PCR carried out in the same procedure and the electrophoresis.

Samples in which the experiment was performed as described above without adding any Hyper-Tth RecA protein and any wild type Tth RecA Protein were produced. After carrying out PCR in the same procedure described above, the samples were subject to electrophoresis and were used as controls.

(Results)

Figure 6:
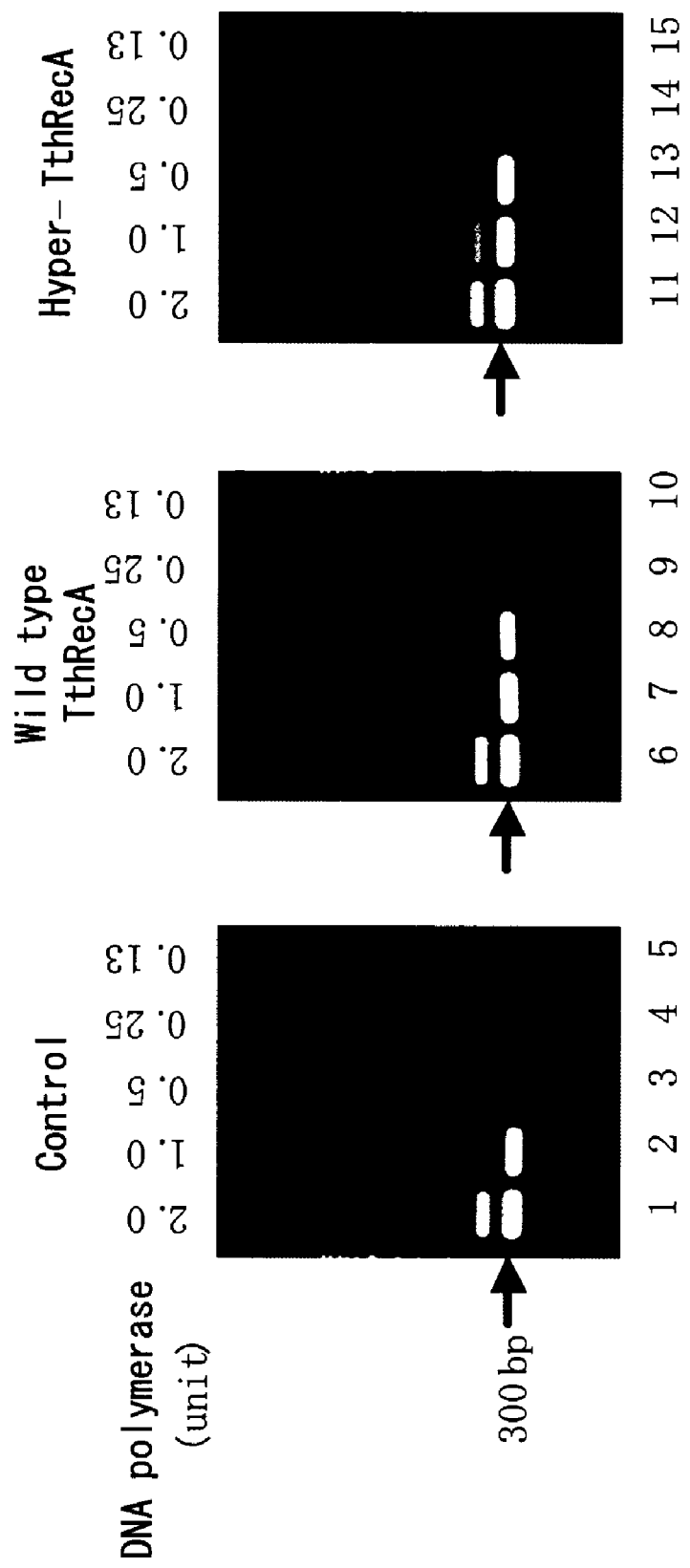
FIG. 6 is a figure showing the example 4 for evaluating the nature of the heat-stable RecA mutant protein of the present invention (amount of DNA polymerase)

The results are shown in FIG. 6.

In FIG. 6, lanes 1-5 are the results of the controls, and show the results of the cases where PCR was carried out using 2.0, 1.0, 0.5, 0.25, and 0.13 units of rTaq DNA Polymerase respectively. In FIG. 6, lanes 6-10 show the results of the cases that PCR is carried out using 2.0, 1.0, 0.5, 0.25, and 0.13 unit of rTaq DNA Polymerase respectively with the wild type TthRecA protein added.

In FIG. 6, lanes 11-15 show the results of the cases where PCR is carried out using 2.0, 1.0, 0.5, 0.25, and 0.13 units of rTaq DNA Polymerase respectively with the Hyper TthRecA protein added.

From the result of FIG. 6, in case where PCR was carried out when the Hyper-TthRecA protein was added, the amplification products were observed to be up to 0.25 unit of rTaq DNA polymerase (Lane 11 to 15). On the other hand, in case where PCR was carried out when the wild type TthRecA protein was added, the amplification products were observed to be up to 0.5 unit of rTaq DNA polymerase (Lane 6 to 8), however, the amplification products were not observed for 0.25 unit and 0.13 unit of rTaq DNA polymerase (Lane 9 to 10). In the controls, the amplification products were observed to be up to 1.0 unit of rTaq DNA polymerase (Lane 1 to 2), however, the amplification products were not observed for 0.5, 0.25, and 0.13 unit of rTaq DNA polymerase (Lane 3 to 4). From the above-mentioned results, it was found that addition of the Hyper-TthRecA protein allows the reaction to effectively proceed in PCR with the smaller amount of rTaq DNA polymerase, compared to the known PCR reaction. In other words, it was found that the Hyper-TthRecA protein has a function for improving the reaction efficiency of rTaq DNA polymerase.

Example 5

Confirmation of the Nature of the Hyper-Tth RecA Protein—4

In addition to the example 4, an experiment was conducted to evaluate the effect of the Hyper-TthRecA protein on a DNA polymerase in PCR by comparing it with the wild type Tth RecA. In the example, a DNA polymerase derived from *Thermococcus kodakaraensis* was evaluated.

(Method)

The experiment is conducted by carrying out PCR using KOD DNA polymerase (TOYOBO product), which is a DNA polymerase derived from *Thermococcus kodakaraensis* of each concentration: 2.0, 1.0, 0.5, 0.25, and 0.13 unit. Specifically, the PCR reactant mixture (25 µl) was prepared by mixing 25 ng of a human genome DNA serving as a template DNA, 0.4 µg of the Hyper-TthRecA protein which was obtained in the example 1, 0.8 µM (final concentration) of each primer, one of KOD DNA polymerase (TOYOBO product) prepared to 2.0, 1.0, 0.5, 0.25, and 0.13 unit and 0.2 mM (final concentration) of a dNTP mixture with a 1×PCR reaction buffer (TOYOBO product). The same primer set A (primer 3 and 4: SEQ ID No. 7, 8) was used as the example 4 and the same human genome DNA was used as the examples 2 and 4.

Each PCR reactant mixture, which was prepared as described above, was subject to PCR to obtain the amplification productions. PCR was carried out through the following steps: (1) the thermal denaturation conducted at 92° C. for 30 seconds, (2) 35 cycles of the amplification reaction (1 cycle: for 10 seconds at 94° C., for 30 seconds at 55° C., for 60 seconds at 68° C.), (3) 1 cycle of the final reaction (1 cycle: for 3 minutes at 68° C.).

After the amplification, an electrophoresis loading buffer was added to each amplification reactant to be stirred. Half of the solution was taken and was subject to 1.2% agarose gel electrophoresis. After the electrophoresis, the gel was stained with ethidium bromide to visualize DNA bands.

Instead of the Hyper-TthRecA protein, the wild type TthRecA protein was added the PCR reactant mixture and the reactant mixture was subject to PCR carried out in the same procedure and the electrophoresis.

Samples in which the experiment was performed as described above without adding any Hyper-Tth RecA protein and any wild type Tth RecA Protein were produced. After carrying out PCR in the same procedure described above, the samples were subject to electrophoresis and were used as controls.

(Results)

Figure 7:
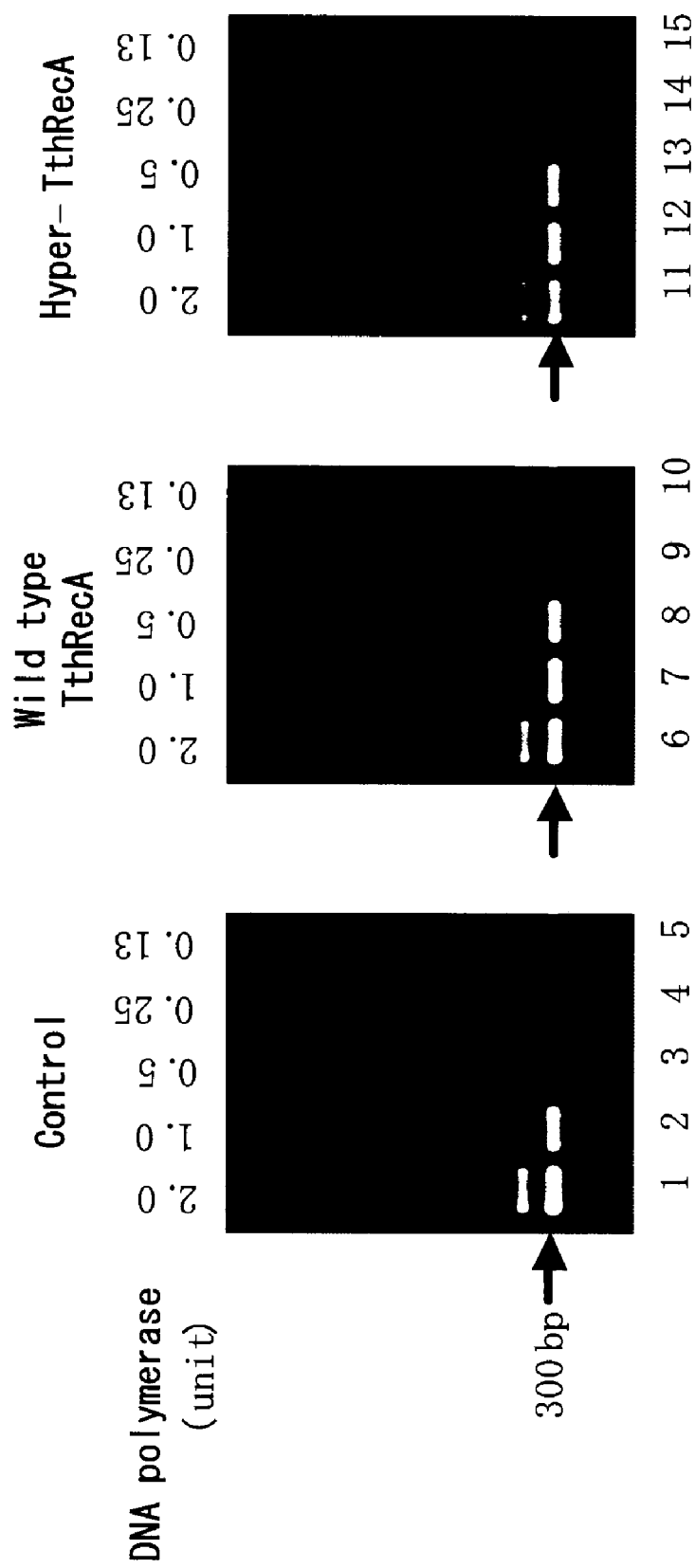
FIG. 7 is a figure showing the example 5 for evaluating the nature of the heat-stable RecA mutant protein of the present invention (amount of DNA polymerase)

The results are shown in FIG. 7.

In FIG. 7, lanes 1-5 are the results of the controls, and show the results of the cases where PCR was carried out using 2.0, 1.0, 0.5, 0.25, and 0.13 units of KOD DNA Polymerase respectively.

In FIG. 7, lanes 6-10 show the results of the cases where PCR was carried out using 2.0, 1.0, 0.5, 0.25, and 0.13 unit of r KOD DNA Polymerase respectively with the wild type TthRecA protein added.

In FIG. 7, lanes 11-15 show the results of the cases where PCR was carried out using 2.0, 1.0, 0.5, 0.25, and 0.13 unit of KOD DNA Polymerase respectively with the Hyper TthRecA protein added.

From the result of FIG. 7, in case that PCR was carried out with the Hyper-TthRecA protein added, the amplification products were observed to be up to 0.25 unit of KOD DNA polymerase (Lane 11 to 15). On the other hand, in case that PCR was carried out with the wild type TthRecA protein added, the amplification products were observed to be up to 0.5 unit of KOD DNA polymerase (Lane 6 to 8), however, the amplification products were not observed for 0.25 unit and 0.13 unit of KOD DNA polymerase (Lane 9 to 10). In the controls, the amplification products were observed to be up to 1.0 unit of KOD DNA polymerase (Lane 1 to 2), however, the amplification products were not observed for 0.5, 0.25, and 0.13 unit of rTaq DNA polymerase (Lane 3 to 5). From the above-mentioned results, it was found that addition of the Hyper-TthRecA protein allows the reaction to effectively proceed in PCR with the smaller amount of KOD DNA polymerase, compared to the known PCR reaction. In other words, it was found that the Hyper-TthRecA protein had a function for improving the reaction efficiency of KOD DNA polymerase. In addition to the result of the example 5, it was understood that the Hyper-TthRecA protein improved the function of DNA Polymerase regardless of the type.

Example 6

Confirmation of the Nature of the Hyper-Tth RecA Protein—5

In addition to the examples 4 and 5, an experiment was conducted to evaluate the effect of the Hyper-TthRecA protein on a DNA polymerase in PCR by comparing it with the wild type Tth RecA. In the example, similarly to the example 5, a DNA polymerase derived from *Thermococcus kodakaraensis* was evaluated in term of concentration of the primers.
(Method)

The primers of each concentration: 1.28, 0.64, 0.32, 0.16, 0.08, 0.04, and 0.02 µM were used for the evaluation. Specifically, the PCR reactant mixture (25 µl) was prepared by mixing 25 ng of a human genome DNA serving as a template DNA, 0.4 µg of the Hyper-TthRecA protein obtained in the example 1, each primer of the concentration prepared to 1.28, 0.64, 0.32, 0.16, 0.08, 0.04 and 0.02 µM (final concentration), 2.0 unit of KOD DNA polymerase (TOYOBO product) and 0.2 mM of a dNTP mixture with a 1×PCR reaction buffer (TOYOBO product). The same human genome DNA was used as the examples 2, 4 and 5.

As the primers, the primer set D (primers 9, 10: SEQ ID No. 13, 14) used in the example 2 was also used to prepare the PCR reactant mixture.

Primer set D
  Primer 9
  5'-aacctcacaaccttggctga-3' (SEQ ID No. 13)
  Primer 10
  5'-ttcacaacttaagatttggc-3' (SEQ ID No. 14)

Each PCR reactant mixture which was prepared as described above was subject to PCR to obtain the amplification productions. PCR was carried out though the following steps: (1) the thermal denaturation conducted at 92° C. for 30 seconds, (2) 35 cycles of the amplification reaction (1 cycle: for 10 seconds at 94° C., for 30 seconds at 55° C., for 60 seconds at 68° C.), (3) 1 cycle of the final reaction (1 cycle: for 3 minutes at 68° C.).

After the amplification, an electrophoresis loading buffer was added to each amplification reactant to be stirred. Half of the solution was taken and was subject to 1.2% agarose gel electrophoresis. After the electrophoresis, the gel was stained with ethidium bromide to visualize DNA bands.

Instead of the Hyper-TthRecA protein, the wild type TthRecA protein is added to the PCR reactant mixture, and the reactant mixture was subject to PCR carried out in the same procedure and the electrophoresis.
(Result)

Figure 8:
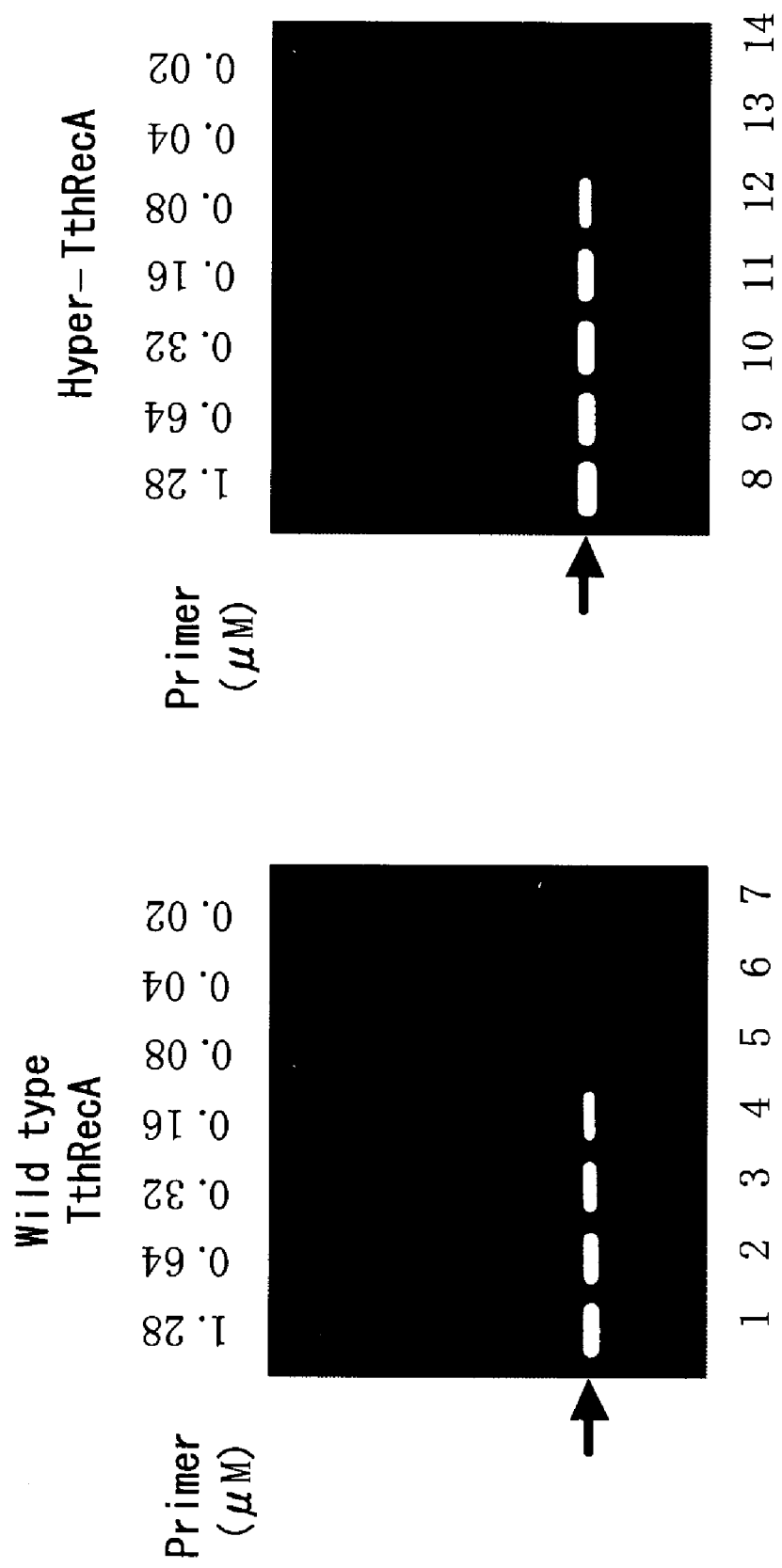
FIG. 8 is a figure showing the example 6 for evaluating the nature of the heat-stable RecA mutant protein of the present invention (amount of primer)

The results are shown in FIG. 8.

In FIG. 8, lanes 1-7 show the results of the cases where PCR is carried out using the primer of the concentration 1.28, 0.64, 0.32, 0.16, 0.08, 0.04, and 0.02 µM respectively with the wild type TthRecA protein added.

In FIG. 8, lanes 8-16 show the results of the cases where PCR was carried out using the primer of the concentration 1.28, 0.64, 0.32, 0.16, 0.08, 0.04, and 0.02 µM respectively with the Hyper TthRecA protein added.

From the result of FIG. 8, in case that PCR was carried out with the Hyper-TthRecA protein added, the amplification products were observed to be up to 0.04 µM of the primers (Lane 8 to 13). On the other hand, in case where PCR was carried out with the wild type TthRecA protein added, the amplification products were observed to be up to 0.08 µM of the primers (Lane 1 to 5), however, the amplification products were not observed for 0.04 and 0.02 µM of the primers (Lane 6 to 7). From the above-mentioned results, it was found that addition of the Hyper-TthRecA protein allows the reaction to effectively proceed in PCR with the smaller amount of the primers, compared to the known PCR reaction. In other words, it was found that the Hyper-TthRecA protein had a function for improving the reaction efficiency of the DNA polymerase. The results match the results of the examples 4 and 5.

Example 7

Confirmation of the Nature of the Hyper-Tth RecA Protein—6

An experiment was conducted to evaluate the effect of the Hyper-TthRecA protein on the annealing temperature of a DNA polymerase in PCR by comparing it with the wild type Tth RecA.
(Method)

The PCR reactant mixture (25 µl) was prepared by mixing 25 ng of a human genome DNA serving as a template DNA, 0.4 µg of Hyper-TthRecA protein which was obtained in the example 1, 0.6 µM (final concentration) of each primer, 2.0 unit of a KOD DNA polymerase (TOYOBO product) and 0.2 mM (final concentration) of a dNTP mixture with a 1×KOD-Plus reaction buffer (TOYOBO product). The same human genome DNA was used as the examples 2, 4 and 6.

The PCR reactant mixture was prepared using 5 kinds of primer sets described below.

Primer set E
  Primer 11
  5'-taataaacttgttcccagat-3' (SEQ ID 16)
  Primer 12
  5'-aggagaaagagcagtgggag-3' (SEQ ID 17)
Primer set F
  Primer 13
  5'-gataagtggaactttagtgt-3' (SEQ ID 18)
  Primer 14
  5'-cataagcattacactgcgca-3' (SEQ ID 19)
Primer set G
  Primer 15
  5'-atacctaaggctctactgca-3' (SEQ ID 20)
  Primer 16
  5'-aggcaatggcggcacccatc-3' (SEQ ID 21)
Primer set H
  Primer 17
  5'-atttctggcctccaacgtta-3' (SEQ ID 22)
  Primer 18
  5'-ccagaaatgcaggcaattgt-3' (SEQ ID 23)
Primer set I
  Primer 19
  5'-tgagcccatcctgaattcc-3' (SEQ ID 24)
  Primer 20
  5'-cagaatggttgtgtagcgca-3' (SEQ ID 25)

The PCR reactant mixtures prepared as described above were subject to PCR under two different conditions to obtain the respective amplification products. The reaction condition I is different from the reaction condition II in the annealing temperatures. The annealing temperature was set to 58° C. in the reaction condition I and the annealing temperature was set to 63° C. in the reaction condition II.

Reaction condition I
  (for 30 seconds at 92° C.)×1 cycle
  (for 10 seconds at 94° C., for 30 seconds at 58° C., for 60 seconds at 68° C.)×35 cycles
  (68° C. for 3 minutes at 68° C.)×1 cycle Reaction condition II
  (for 30 seconds at 92° C.)×1 cycle
  (for 10 seconds at 94° C., for 30 seconds at 63° C., for 60 seconds at 68° C.)×35 cycles
  (for 3 minutes at 68° C.)×1 cycles After the amplification, an electrophoresis loading buffer was added to each amplification reactant to be stirred. Half of the solution was taken and was subject to 1.2% agarose gel electrophoresis. After the electrophoresis, the gel was stained with ethidium bromide to visualize DNA bands.

Instead of the Hyper-TthRecA protein, the wild type TthRecA protein was added to the PCR reactant mixture and the reactant mixture was subject to PCR carried out in the same procedure and the electrophoresis.

(Result)

The results are shown in FIG. 9.

In FIG. 9, lanes 1-5 are the results of the experiment in which PCR was carried out using the primer set E, F, G, H, and I respectively in the presence of the wild type TthRecA protein. At that time, the annealing temperature was set at 58° C.

In FIG. 9, lanes 6-10 are the results of the experiment in which PCR was carried out using the primer set E, F, G, H, and I respectively in the presence of the Hyper type TthRecA protein. At that time, the annealing temperature was set at 58° C.

In FIG. 9, lanes 11-15 are the results of the experiment in which PCR was carried out using the primer set E, F, G, H, and I respectively in the presence of the wild type TthRecA protein. The annealing temperature was set at 63° C.

In FIG. 9, lanes 16-20 are the results of the experiment in which PCR was carried out using the primer set E, F, G, H, and I respectively in the presence of the Hyper type TthRecA protein. At that time, the annealing temperature was set at 63° C.

From the results of FIG. 9, in case that PCR was carried out with the Hyper-TthRecA protein added, the amplification products were observed at high annealing temperature (Lane 16 to 20). Particularly, when the annealing temperature was set to 58° C., the amplification products were not observed in PCR using the primer set E. However, it is noticeable that the amplification products were observed in PCR using the primer set E when the annealing temperature was raised (comparison between lane 6 and lane 16). On the other hand, in case that PCR was carried out with the wild type TthRecA protein added, the amplification products were not observed when the annealing temperature was increased to 63° C. (lane 11 to 15). From those results, it was found that the addition of the Hyper-TthRecA protein allows PCR to be carried out at the higher annealing temperature, compared to a known PCR. It is known that when PCR is carried out at the high annealing temperature, the binding capacity of the primers which are template specific improves, however, the primers do not bind to the template nucleic acids when the annealing temperature is very high. Therefore, it is understood that the addition of the RecA mutant protein of the present invention allows the annealing temperature to be set at a high temperature and thus, the misannealing reaction of the primers are decreased to improve the accuracy of PCR.

The present invention provides a nucleic acid amplification method which is useful in the medical field, the biochemical field, the environmental field, the food field and the like.

According to the examples of the present invention, it is possible to mass produce the heat-stable RecA mutant protein by using a genetic engineering techniques for industrial use.

According to the examples of the present invention, it is possible to eliminate other proteins derived from host cell. Thus, it is possible to mass produce reliable enzymes easily.

The principles, of the preferred examples and mode of operation of the present invention have been described in the foregoing specification. However, the invention, which is intended to be protected, is not to be construed as limited to the particular example disclosed. Further, the example described herein is to be regarded as illustrative rather than restrictive. Variations and changes may be made by others, and equivalents employed, without departing from the spirit of the present invention. Accordingly, it is expressly intended that all such variations, changes and equivalents that fall within the spirit and scope of the present invention as defined in the claims, be embraced thereby.

The invention claimed is:

1. A mutant heat-stable Recombinase A (RecA) protein, comprising SEQ ID NO:4, except that at least one amino acid at position 328 to 340 of SEQ ID NO: 4 is deleted or substituted with a different amino acid; wherein the mutant heat-stable RecA protein has a function of providing a decreased mis-annealing of nucleotide(s) to a template nucleic acid, compared to the wild type heat-stable RecA protein of SEQ ID NO:4, under identical polymerase chain reaction (PCR) DNA amplification conditions.

2. The mutant heat-stable RecA mutant protein according to claim 1, wherein the residues 328-340 of SEQ ID NO:4 are deleted.

3. The mutant heat-stable RecA protein according to claim 1, wherein an acidic amino acid at positions 328 to 340 of SEQ ID NO:4 is substituted or deleted.

4. The mutant heat-stable RecA protein according to claim 1 which consist of the polypeptide as set forth in SEQ ID NO:2.

5. A nucleic amplification kit suitable for amplifying a nucleic acid, comprising the mutant heat-stable RecA protein according to claim 1 and a thermostable deoxyribonucleic acid (DNA) polymerase.

6. A nucleic amplification kit suitable for amplifying a nucleic acid, comprising the mutant heat-stable RecA protein according to claim 2 and a thermostable deoxyribonucleic acid (DNA) polymerase.

7. A nucleic amplification kit suitable for amplifying a nucleic acid, comprising the mutant heat-stable RecA protein according to claim 3 and a thermostable deoxyribonucleic acid (DNA) polymerase.

8. A nucleic amplification kit suitable for amplifying a nucleic acid, comprising the mutant heat-stable RecA protein according to claim 4 and a thermostable deoxyribonucleic acid (DNA) polymerase.

9. A mutant heat-stable Recombinase A (RecA) protein, comprising SEQ ID NO:4, except that at least one amino acid at position 328 to 340 of SEQ ID NO: 4 is deleted or substituted with a different amino acid; wherein the mutant heat-stable RecA protein has a function of providing a decreased mis-annealing of nucleotide(s) to a template nucleic acid, compared to the wild type heat-stable RecA protein of SEQ ID NO:4, under identical polymerase chain reaction (PCR) DNA amplification conditions.

10. A nucleic amplification kit suitable for amplifying a nucleic acid, comprising the mutant heat-stable RecA protein according to claim 9 and a thermostable deoxyribonucleic acid (DNA) polymerase.

* * * * *